(12) United States Patent
Pearce et al.

(10) Patent No.: US 11,768,210 B2
(45) Date of Patent: Sep. 26, 2023

(54) PORTABLE COAGULATION MONITORING DEVICES, SYSTEMS, AND METHODS

(71) Applicant: Entegrion, Inc., Durham, NC (US)

(72) Inventors: Matthew Pearce, Chester (GB); Richard Hall, Chester (GB); Joseph Anthony DaCorta, Chapel Hill, NC (US)

(73) Assignee: Entegrion, Inc., Durham, NC (US)

(*) Notice: Subject to any disclaimer, the term of this patent is extended or adjusted under 35 U.S.C. 154(b) by 441 days.

(21) Appl. No.: 16/990,661

(22) Filed: Aug. 11, 2020

(65) Prior Publication Data

US 2020/0371121 A1 Nov. 26, 2020

Related U.S. Application Data

(60) Division of application No. 14/717,117, filed on May 20, 2015, now Pat. No. 10,739,358, which is a continuation of application No. PCT/US2014/065882, filed on Nov. 17, 2014, and a continuation-in-part of application No. 13/897,712, filed on May 20, 2013, now Pat. No. 9,063,161,
(Continued)

(51) Int. Cl.
*G01N 33/86* (2006.01)
*G01N 33/49* (2006.01)
*G01N 11/00* (2006.01)

(52) U.S. Cl.
CPC ......... *G01N 33/86* (2013.01); *G01N 33/4905* (2013.01); *G01N 2011/008* (2013.01)

(58) Field of Classification Search
CPC ......... G01N 33/4905; G01N 2011/008; G01N 33/86; G01N 21/17
See application file for complete search history.

(56) References Cited

U.S. PATENT DOCUMENTS 5,181,415 A 1/1993 Esvan et al.
5,223,227 A * 6/1993 Zuckerman .......... G01N 11/162
422/547

(Continued)

OTHER PUBLICATIONS

R. G. Horn (Addition of a polarizing microscope to the Weissenberg Rheogoniometer, Rev. Sci. Instrum, 50(5), May 1979 (Year: 1979).*
(Continued)

*Primary Examiner* — Dean Kwak
(74) *Attorney, Agent, or Firm* — Eversheds Sutherland (US) LLP; Christopher C. Bolten; Albert K. Heng

(57) ABSTRACT

Portable coagulation monitoring devices, systems, and methods are disclosed. Namely, a test cartridge is provided for use in a portable coagulation monitor (PCM) device. Further, the test cartridge comprises two glass-filled thermoplastic polymer plates and a disposable blood introduction device. The two glass-filled thermoplastic polymer plates are arranged substantially in parallel with a small gap therebetween for receiving a sample of blood to be tested. Using the PCM device, the two glass-filled thermoplastic polymer plates can be moved linearly relative to each other. Methods of measuring coagulation response in a blood sample using the test cartridge and the PCM device are provided. A method of introducing blood into the test cartridge using the disposable blood introduction device is provided.

34 Claims, 25 Drawing Sheets

Related U.S. Application Data which is a division of application No. 12/971,013, filed on Dec. 17, 2010, now Pat. No. 8,450,078.

(60) Provisional application No. 61/904,523, filed on Nov. 15, 2013, provisional application No. 61/904,489, filed on Nov. 15, 2013, provisional application No. 61/287,780, filed on Dec. 18, 2009.

(56) References Cited

U.S. PATENT DOCUMENTS

| | | |
|---|---|---|
| 5,629,209 A | 5/1997 | Braun, Sr. |
| 5,838,515 A | 11/1998 | Mortazavi et al. |
| 6,060,323 A | 5/2000 | Jina |
| 6,495,367 B1 | 12/2002 | Isogawa et al. |
| 7,005,857 B2 | 2/2006 | Stiene |
| 7,074,582 B2 | 7/2006 | Fischer |
| 7,117,721 B2 | 10/2006 | Neel et al. |
| 7,361,306 B2 | 4/2008 | Bote Bote |
| 7,399,637 B2 | 7/2008 | Wright et al. |
| 2003/0083686 A1 | 5/2003 | Freeman |
| 2003/0130596 A1 | 7/2003 | Von Der Goltz |
| 2004/0072357 A1 | 4/2004 | Stiene et al. |
| 2004/0175296 A1 | 9/2004 | Opalsky et al. |
| 2005/0015001 A1 | 1/2005 | Lee et al. |
| 2005/0180886 A1 | 8/2005 | Bote Bote |
| 2005/0233460 A1 | 10/2005 | Clague et al. |
| 2005/0233466 A1 | 10/2005 | Wright et al. |
| 2009/0185734 A1 | 7/2009 | Lindberg et al. |
| 2011/0135698 A1 | 6/2011 | Lundquist et al. |
| 2011/0151491 A1 | 6/2011 | Dennis et al. |
| 2011/0201099 A1* | 8/2011 | Anderson ............... G01N 1/10 422/68.1 |
| 2012/0028342 A1* | 2/2012 | Ismagilov ............... C12Q 1/703 422/503 |
| 2012/0028822 A1 | 2/2012 | Joseph et al. |
| 2012/0107851 A1 | 5/2012 | Killard et al. |
| 2013/0267017 A1 | 10/2013 | Dennis et al. |

OTHER PUBLICATIONS

U.S. Appl. No. 12/971,013 / U.S. Pat. No. 8,450,078, filed Dec. 17, 2010 / May 28, 2013.

U.S. Appl. No. 13/897,712 / U.S. Pat. No. 9,063,161, filed May 20, 2013 / Jun. 23, 2015.

U.S. Appl. No. 14/717,117 / U.S. Pat. No. 10,739,358, filed May 20, 2015 / Aug. 11, 2020.

Goto et al. "Characterization of the unique mechanism mediating the shear-dependent binding of soluble von Willebrand factor to platelets", JBC, 1995, 270(40): 23352-23361.

Moake et al. "Invovement of large plasma von Willebrand factor (vWF) multimers and unusually large vWF forms derived from endothelial cells in shear stress-induced platelet aggregation", J. Clin. Invest., 1986, 78:1456-1461.

Horn, "Addition of a polarizing microscope to the Weissenberg Rheogoniometer", Rev. See. Instrum., 1979,659-661.

Hansson et al. "Whole blood coagulation on protein adsorption-resistant PEG and peptide functionalised PEG-coated titanium surfaces", Biomaterials, 2005, 26:861-872.

Nam et al. "Evaluation of the Roche CoaguChek XS handheld coagulation analyzer in a cardiac outpatient clinic", Annuals of Clinical & Laboratory Science, 38(1 ):37-40.

Glover CJ et al.: "Mechanical trauma effect on clot structure formation", Thrombosis Research. Tarrytown, NY, US. vol. 10. No. 1, Jan. 1, 1977, pp. 11-25, XP0228T1328.

Kaibara et al "Rheological studies on blood coagulation and network formation of fibrin", Polymer Gels and Networks, Elsevier Amsterdam, NL, vol. 2, No. 1, Jan. 1, 1994, pp. 1-28, XP024175674.

Extended European Search Report dated Aug. 1, 2013 in EP Patent Appl. Serial No. 10838275.5, 5 pages.

Extended European Search Report dated Aug. 1, 2017 in EP Patent Appl. Serial No. 14861634.5, 7 pages.

International Search Report & Written Opinion dated Aug. 23, 2011 in Int'l PCT Patent Appl. Serial No. PCT/US2010/060911, 6 pages.

International Search Report and Written Opinion dated Mar. 25, 2015 in Int'l PCT Patent Appl. Serial No. PCT/US2014/065882, 13 pages.

\* cited by examiner

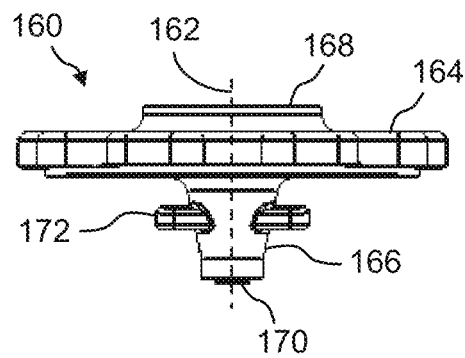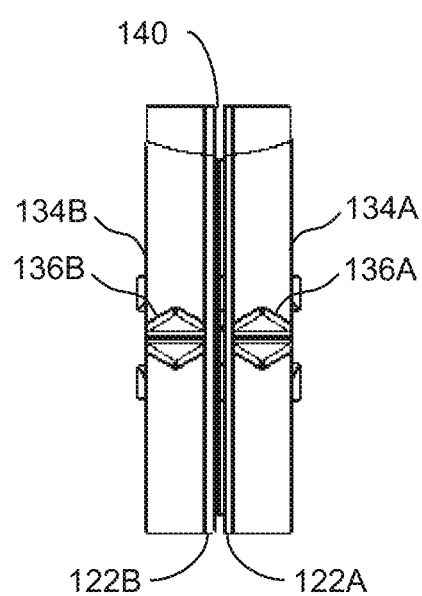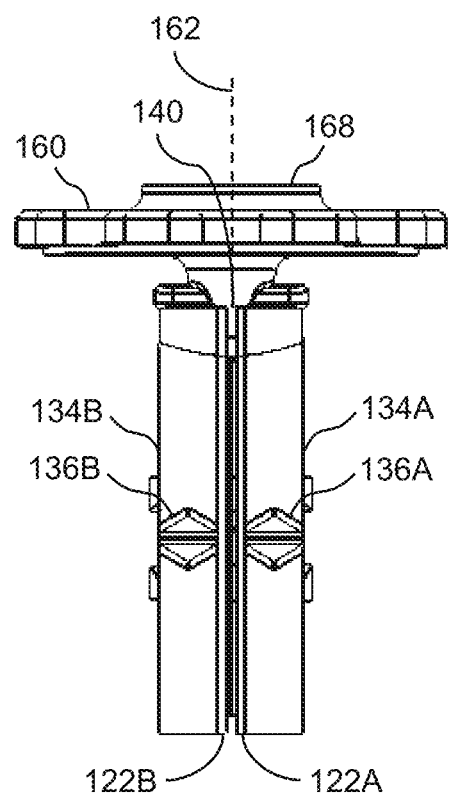
FIG. 10A  FIG. 10B

PORTABLE COAGULATION MONITORING DEVICES, SYSTEMS, AND METHODS

CROSS-REFERENCE TO RELATED APPLICATIONS

This patent application is a divisional of and claims priority to U.S. patent application Ser. No. 14/717,117 entitled "Portable Coagulation Monitoring Devices, Systems, And Methods" filed on May 20, 2015. U.S. patent application Ser. No. 14/717,117 is a continuation of and claims priority to PCT International Patent Application No. PCT/2014/065882 entitled "Portable Coagulation Monitoring Devices, Systems, And Methods" filed on Nov. 17, 2014 and which is related and claims priority to U.S. Provisional Patent Application No. 61/904,523 entitled "Glass-Filled Thermoplastic Polymer Plates for Measurement of Blood Thromboelastography" filed on Nov. 15, 2013 and U.S. Provisional Patent Application No. 61/904,489 entitled "Disposable Blood Introduction System" filed on Nov. 15, 2013. U.S. patent application Ser. No. 14/717,117 is also a continuation-in-part of and claims priority to U.S. patent application Ser. No. 13/897,712 entitled "Portable Coagulation Monitoring Device for Assessing Coagulation Response" filed on May 20, 2013 (now U.S. Pat. No. 9,063,161 issued Jun. 23, 2015) which in turn is a divisional of and claims priority to U.S. patent application Ser. No. 12/971,013 entitled "Portable Coagulation Monitoring Device and Method of Assessing Coagulation Response" filed on Dec. 17, 2010 (now U.S. Pat. No. 8,450,078 issued May 28, 2013) which is related and claims priority to U.S. Provisional Patent Application No. 61/287,780 entitled "Portable Coagulation Monitoring Device, System and Method of Use" filed on Dec. 18, 2009. The entire disclosures of the aforementioned applications are specifically incorporated by reference herein in their entirety.

TECHNICAL FIELD

The presently disclosed subject matter relates generally to blood coagulation monitoring methods and more particularly to portable coagulation monitoring devices, systems, and methods including the use of glass-filled thermoplastic polymer plates and a disposable blood introduction device.

BACKGROUND

The process by which the body prevents blood loss is referred to as coagulation. Coagulation involves the formation of a blood clot (thrombus) that prevents further blood loss from damaged tissues, blood vessels or organs. The formation of a blood clot is a complicated process involving a first system comprised of cells called platelets that circulate in the blood and serve to form a platelet plug over damaged vessels and a second system based upon the actions of multiple proteins (called clotting factors) that act in concert to produce a fibrin clot. These two systems work in concert to form a clot and disorders in either system can yield disorders that cause either too much or too little clotting.

Platelets serve three primary functions: (1) sticking to the injured blood vessel (a phenomenon called platelet adherence); (2) attaching to other platelets to enlarge the forming plug (a phenomenon called platelet aggregation); and (3) providing support for the processes of the coagulation cascade (molecules on the surface of platelets greatly accelerate several key reactions).

When a break in a blood vessel occurs, substances are exposed that normally are not in direct contact with the blood flow. These substances (primarily collagen and attached multimeric von Willibrand factor) allow the platelets to adhere to the broken surface. Once a platelet adheres to the surface, it releases chemicals that attract additional platelets to the damaged area, referred to as platelet aggregation. These two processes are the first responses to stop bleeding. The protein-based system (the coagulation cascade) serves to stabilize the plug that has formed and further seal up the wound.

The support role of the platelet to the coagulation cascade is provided, in part, by one of the components on the outside of a platelet, called phospholipids, which are required for many of the reactions in the clotting cascade. The goal of the cascade is to form fibrin, which will form a mesh within the platelet aggregate to stabilize the clot. All of the factors have an inactive and active form. Once activated, the factor will serve to activate the next factor in the sequence until fibrin is formed. The coagulation cascade takes place at the site of a break in, e.g., a blood vessel that has the platelet aggregate. Fibrin forms a mesh that, in concert with the platelets, plugs the break in the vessel wall. The fibrin mesh is then further stabilized by additional factors which cross-linkup the clot (much like forming an intricate network of reinforced strands of fibrin).

In the case of trauma-induced bleeding, it is important to understand very quickly the clotting response of a particular individual in order to apply appropriate therapy to treat bleeding and ensure that the trauma is dealt with appropriately. Defective platelet functions, both primary (adhesive, von Willibrand factor interaction) and secondary (fibrin polymer organization and polymerization, integrin function) are recognized as a particularly important contributor in prolonged non compressible bleeding. The development of hemostatic disorders in trauma patients, and associated progression in hemorrhagic and other shock states, can be due to different factors and thus require different therapies.

Currently, thromboelastography (TEG) is the accepted clinical standard for testing the efficiency of whole blood coagulation. As an example, the related U.S. Pat. No. 8,450,078, entitled "Portable Coagulation Monitoring Device and Method of Assessing Coagulation Response" (herein incorporated in its entirety) discloses a portable coagulation monitoring device typically comprising glass plates used to diagnose trauma-related coagulopathies in the field. Further, current methods of introducing blood into, for example, a test cartridge of coagulation monitoring devices may involve measuring the amount of blood required for a test by using a pipette or other capillary device, for example, and then pipetting the required amount of blood into the test cartridge. Blood introduction and the need for clinical staff to pipette blood is a challenge in point-of-care settings and operating room settings where sterility is important.

SUMMARY

In one aspect, the present invention discloses a device for measuring coagulation response in a blood sample including: a set of test components that include a first member having a first surface, and a second member having a second surface, the first member positioned for having the first surface facing the second surface of the second member, and spaced an amount sufficient to allow a sample droplet of blood to contact the first surface and the second surface and initiate coagulation, and the first member and second member being linearly movable relative to each other, wherein the first and second members include a glass-filled thermoplastic polymer; a drive mechanism connected to at least one of the first member and the second member for linearly moving the first member and the second member relative to each other in parallel when a blood sample is in contact with the first surface and the second surface; and an optical detection sensor system for detecting interaction of light with a blood sample located between the first member and second member, as an indication of coagulation response of the blood sample.

In some embodiments, the first surface and the second surface are spaced apart from about 50 μm to about 250 μm. Moreover, the glass-filled thermoplastic polymer may be selected from the group consisting of nylon (polyamide), polycarbonate, polypropylene, polyethylene and polyester. The composition of the polymer may include glass beads and/or glass fibers in amounts including glass beads and/or fibers of about 5% to about 60% in some examples, or about 30% in other examples.

In certain other embodiments, at least one of the first or second members may be a rod that can rotate to initiate coagulation. In such examples, the device may further include a third member having a third surface spaced an amount sufficient to allow a sample droplet of blood to contact the surface of the rod and initiate coagulation.

Some aspects of the present disclosure include a blood sample collection cartridge which is removable from the device and within which the test components are housed. This test cartridge may be disposable after use and may further include a memory device for storing data relating to a blood sample tested. The blood sample collection cartridge may also include pinch contact ribs used to securely couple engagement features of the test components with the drive mechanism of the device.

The drive mechanism may be programmed for moving the first member and second member at different speeds relative to each other for detecting different mechanisms involved in a coagulation response of a blood sample. The drive mechanism may include piezo motors or any other suitable driving source. The device may include a microcontroller for controlling operation of the drive mechanism and optical detection sensor system. It may also include a displacement sensor for detecting and controlling the amount of relative movement between the first member and the second member. Further still, the device may include a connection interface module for connecting and communicating between the device and an external system, and an analog to digital converter coupled to the optical detection sensor system for converting analog signals indicative of coagulation response of a blood sample into digital signals for storage thereof. In some embodiments, the device may also include a temperature control mechanism that may include a heater and/or a cooling device.

The optical detector sensor system may be adapted for detecting binding of the blood sample to the first surface and the second surface as an indication of platelet response during coagulation.

In some embodiments, the first and/or second surface has been treated to induce, slow, or modify the coagulation process for selecting in favor of or against specific aspects of coagulation of the sample. The treatments may optionally enhance or reduce at least one characteristic selected from the group consisting of platelet or blood protein binding, reactivity, and activation. In general, the device is configured for analyzing blood rheology and coagulation of fresh whole blood or some fraction thereof without adding external reagents. The device may also be configured for measuring, with no functional delay, the dynamic balance between pro- and anti-thrombotic hemostatic status by sequential samples from the same person or animal.

In certain other embodiments, the device may include a first channel and a second channel, wherein the first channel comprises the set of test components, the drive mechanism, and the optical detection sensor system, and the second channel comprises a second set of test components, a second drive mechanism, and a second optical detection sensor system, and further wherein the first and second channels operate independently of one another and enable the device to perform measurements of two blood samples at the same time. The separate channels may be configured to perform distinct measurements that include any one of a thrombelastogram test, a fibrinogen test, a heparin test, and other platelet function test.

In another aspect, the present invention discloses a method of measuring coagulation response in a blood sample including the steps of: placing a sample droplet of blood between and in contact with first and second facing surfaces of oppositely disposed glass-filled thermoplastic polymer members; moving at least one member linearly with respect to the other member at a predetermined speed sufficient to activate platelets through exposure to shear forces; and optically detecting, via measurement of mechanical displacement, the interaction between the first and second surfaces resulting from changes in the viscosity of the sample fluid and binding to the member surfaces in order to measure coagulation response of the droplet of blood. In some aspects, two blood sample collection cartridges are used, wherein the first set of test components are housed in a first cartridge representing part of a first channel and the second set of test components are housed in a second cartridge representing part of a second channel.

In some aspects, the device may also include a humidity control mechanism. In one example, the humidity control mechanism may include a sponge-like pad inside a humidity pouch. The humidity pouch may also include a removable cover, thereby enabling the cover to be optionally removed to expose the sponge-like pad to an interior environment of the device.

In a further aspect, the present invention discloses a method of measuring coagulation response in a blood sample including the steps of: placing a sample droplet of blood between and in contact with a first surface and a second surface of oppositely disposed glass-filled thermoplastic polymer members; moving at least one member linearly with respect to the other member at a predetermined speed sufficient to activate platelets through exposure to shear forces; and optically detecting, via measurement of mechanical displacement, the interaction between the first and second surfaces resulting from changes in the viscosity of the sample fluid and binding to the member surfaces in order to measure coagulation response of the droplet of blood. In some embodiments, at least one member may be moved at a first speed and optically detecting adherence of the sample droplet of blood to the surface of the members to determine platelet response during coagulation. The method may also include subsequently moving at least one member at a second speed slower than the first speed, and optically detecting the level of coagulation of the blood sample as indicative of fibrin polymerization response.

The relative motion between the two members may be controlled to generate arbitrarily selected waveforms to induce desired fluid shear rates at selected amplitudes, frequency, duration, and sequence such that the device is enabled to emulate fluid shear as desired over a broad range including from about DC (zero shear) to shear rates that would cause fluid cavitation and subsequent destruction of the cellular components of the sample, and continuously including all points in the shear rate spectrum between these two points. The shear rate may also be controlled in a sequence of values to generate specific protocols or plate motion paradigms for targeted diagnostic or analytic objectives, wherein such targeted diagnostic or analytic objectives include rapid initiation of primary coagulation, destructive or non-destructive viscoelastic evaluation of early, mid-phase, or late-phase clotting, emulation of clinically-accepted or otherwise recognized shear rate protocols for comparison with other commercial or experimental devices, or validation testing against known standards.

Optical detection may be conducted by transmitting electromagnetic waves into the sample droplet, and detecting at least one of transmission, absorption, reflection and refraction of the electromagnetic waves through the sample droplet at respective light detectors, to generate analog signals representative of coagulation properties of the blood in the sample droplet for primary and secondary coagulation mechanisms. The signals may also be converted to digital signals, stored, and analyzed in a predetermined manner to obtain selected information about the coagulation response of the blood in the sample droplet.

In some embodiments, the method may include moving one member relative to the other member in a manner causing the other member to move due to visco elastic coupling between the blood and the other member; and determining the visco elastic properties of the blood from the movement of the other member. The method may also include detecting strain rates caused by movement of the one member and the other member caused by visco elastic coupling between the one member and the other member caused by the blood sample; and determining the coagulation state of the blood by inference analysis based on visco elasticity of the blood sample determined from mechanical coupling between the two members and the resulting strain rates. The visco elasticity of the blood may be continually measured over time to monitor changes of the coagulation response of the blood.

In a further aspect, the present invention discloses a method of measuring coagulation response in a blood sample including the steps of: placing a sample droplet of blood between and in contact with facing surfaces of oppositely disposed glass-filled thermoplastic polymer members; moving at least one member linearly with respect to the other member at a first speed; optically detecting a first coagulation response of the blood indicative of platelet response in the blood; moving at least one member linearly with respect to the other member at a second speed; and optically detecting a second coagulation response of the blood indicative of fibrin polymerization.

Other aspects of the present invention include a test cartridge for use with a device for measuring coagulation response in a blood sample that includes a first member having a first surface, and a second member having a second surface, the first member positioned for having the first surface facing the second surface of the second member, and spaced an amount sufficient to allow a sample droplet of blood to contact the first surface and the second surface and initiate coagulation, and the first member and second member being linearly movable relative to each other, wherein the first and second members comprise a glass-filled thermoplastic polymer.

Other aspects further include a receptacle in the test cartridge for a blood introduction mechanism wherein the receptacle provides a path for the sample droplet of blood to pass form the blood introduction mechanism to a point between the first surface and the second surface. The blood introduction mechanism may include an open top; a funnel portion; a flat bottom; and a lip attached to the funnel portion; wherein the open top comprises an opening larger than an opening at the flat bottom, and further wherein a desired amount of blood introduced to the open top may pass through the blood introduction mechanism and into the receptacle of the test cartridge, thereby providing the sample droplet of blood into the device. The blood introduction mechanism may also include a solid plug cap attached wherein the solid plug cap sealingly nests within the opening of the open top. The mechanism may further include one or more alignment features disposed on the funnel portion.

Certain aspects of the presently disclosed subject matter having been stated hereinabove, which are addressed in whole or in part by the presently disclosed subject matter, other aspects will become evident as the description proceeds when taken in connection with the accompanying Drawings as best described herein below.

BRIEF DESCRIPTION OF THE DRAWINGS

Figure 1:
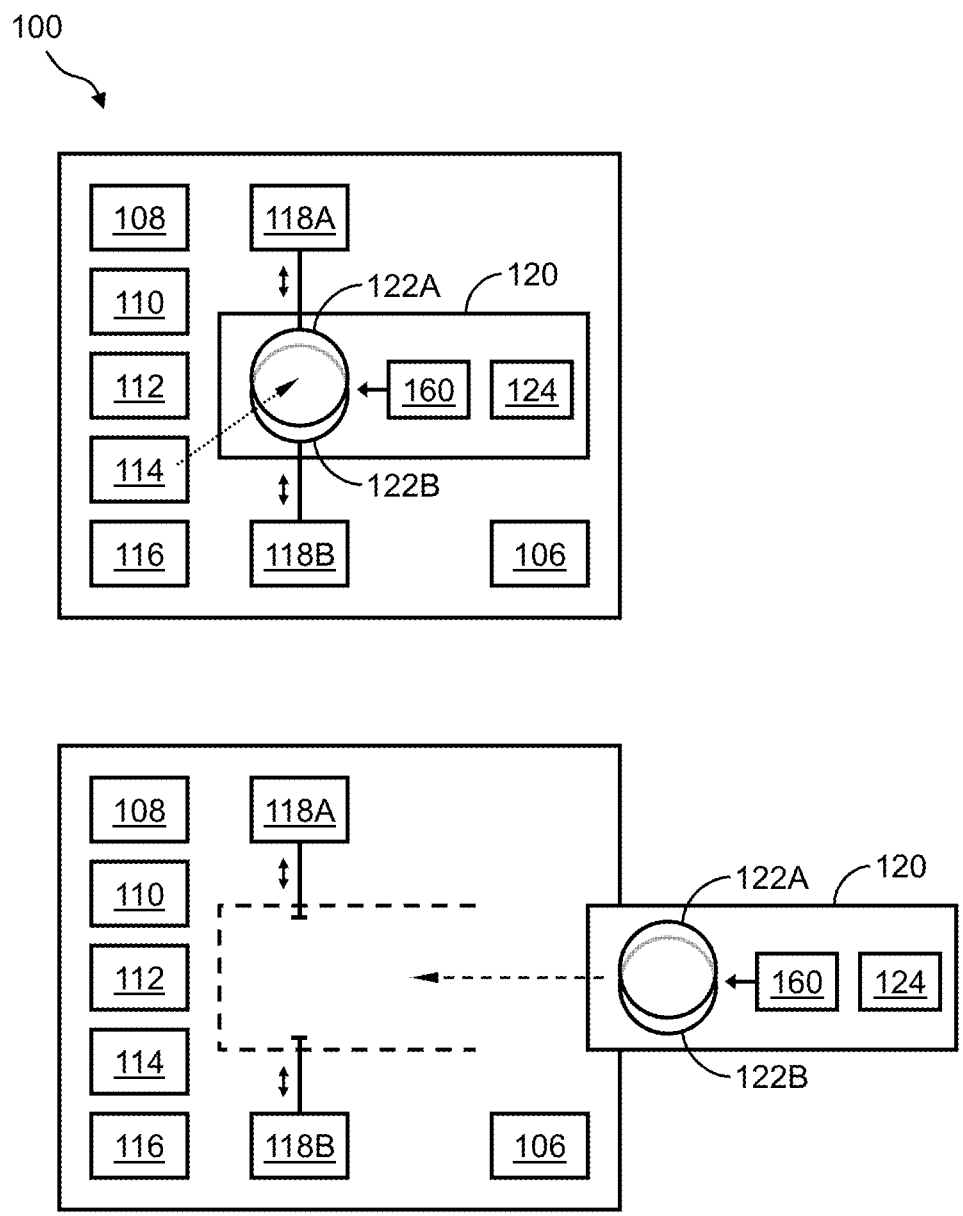
Figure 2A:
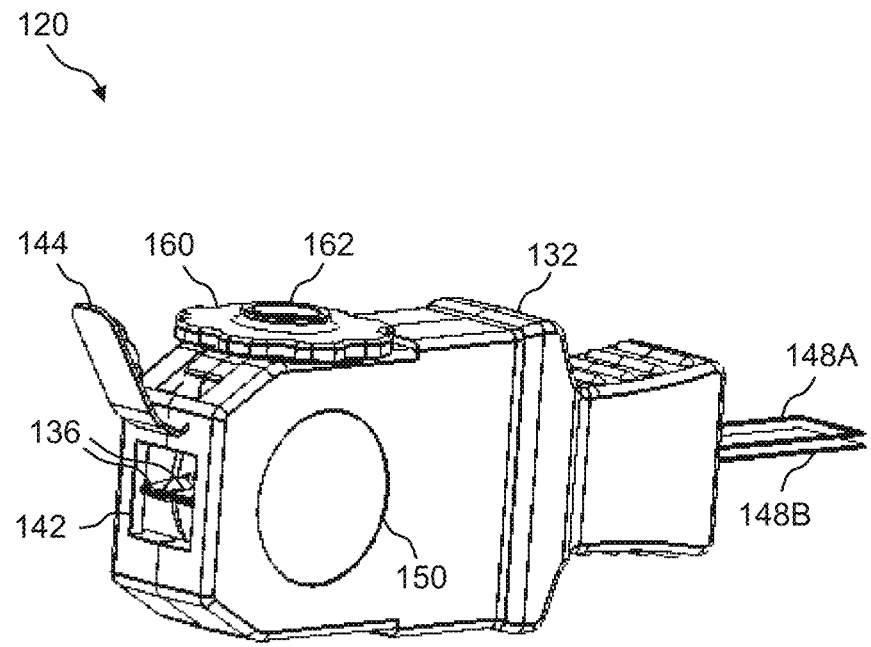
Figure 2B:
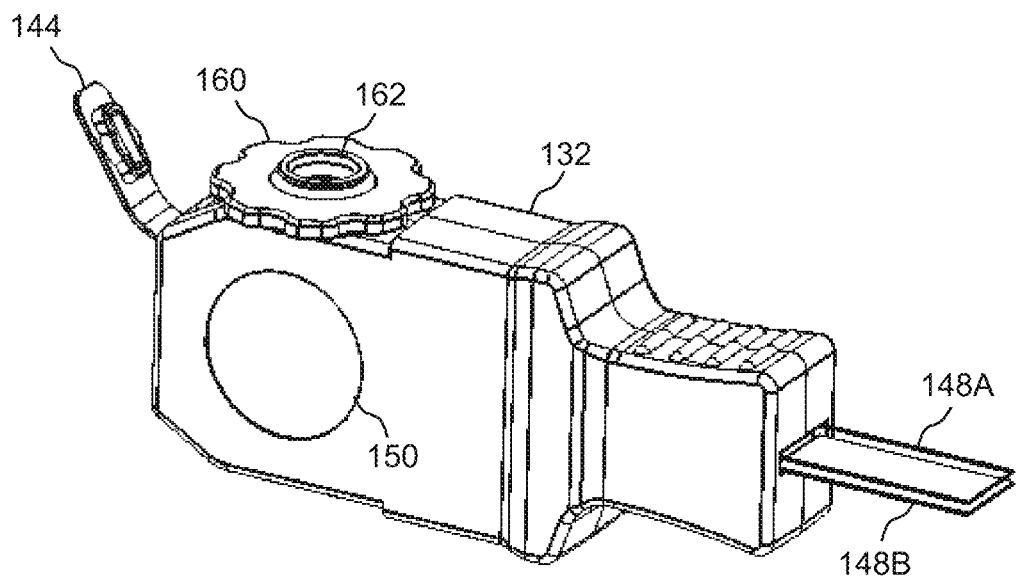
Figure 3A:
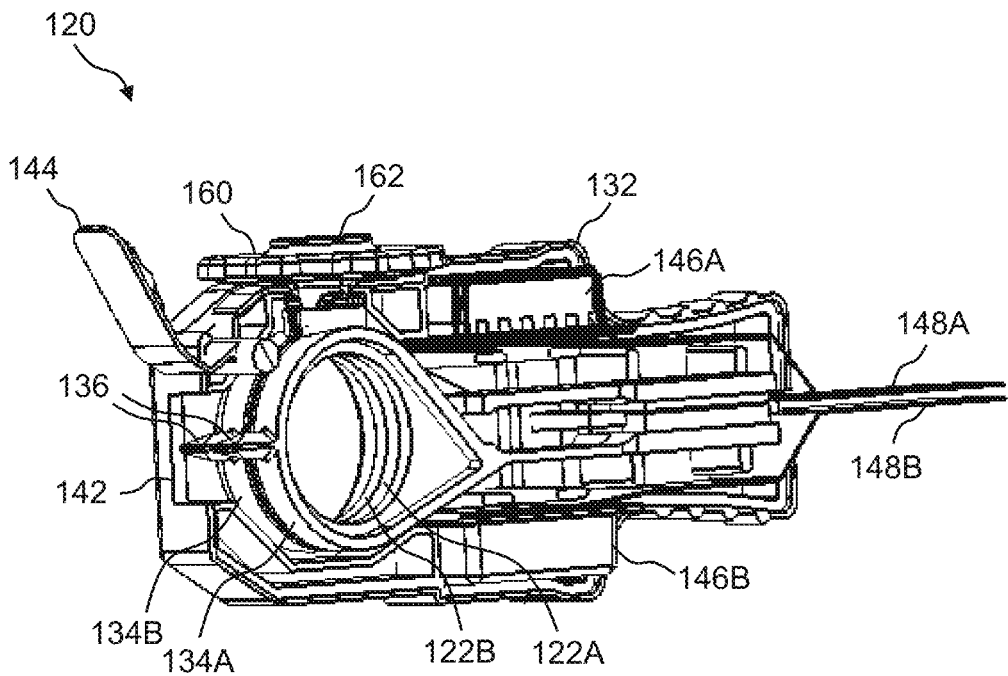
Figure 3B:
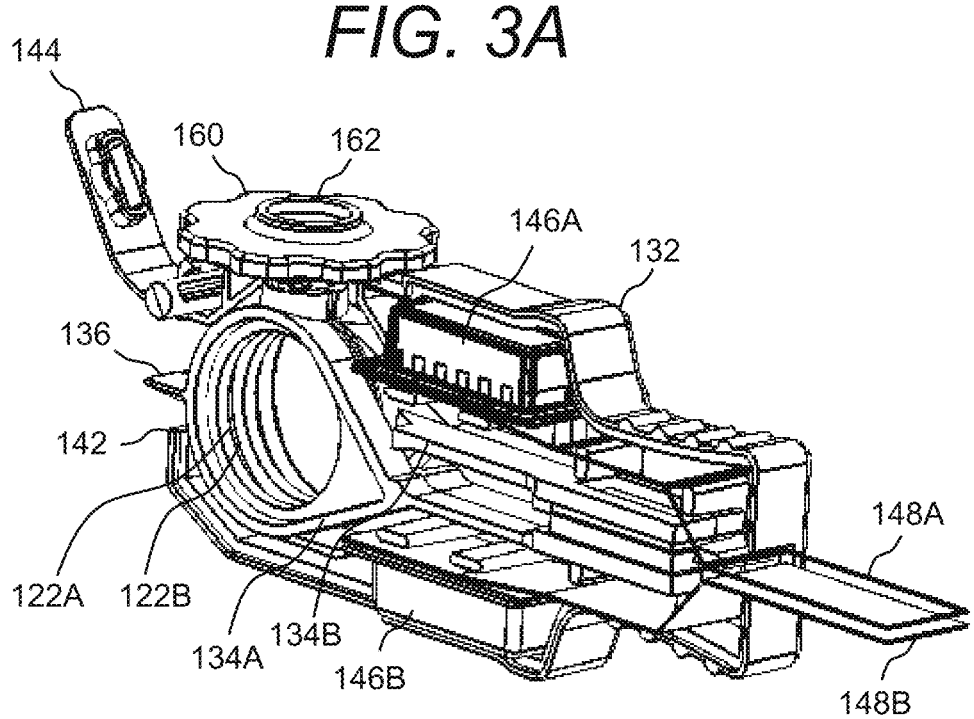
Figure 4A:
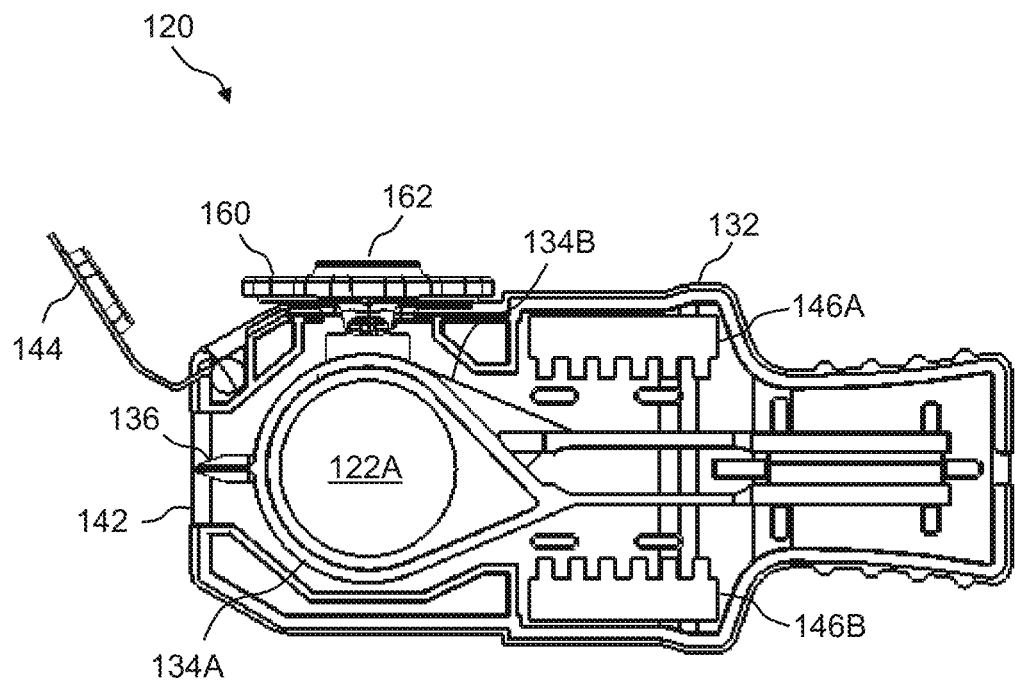
Figure 4B:
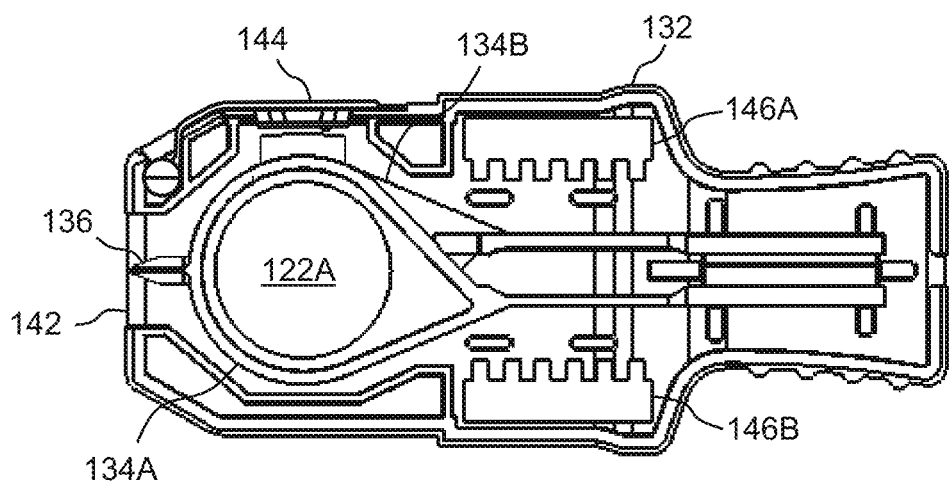
Figure 5A:
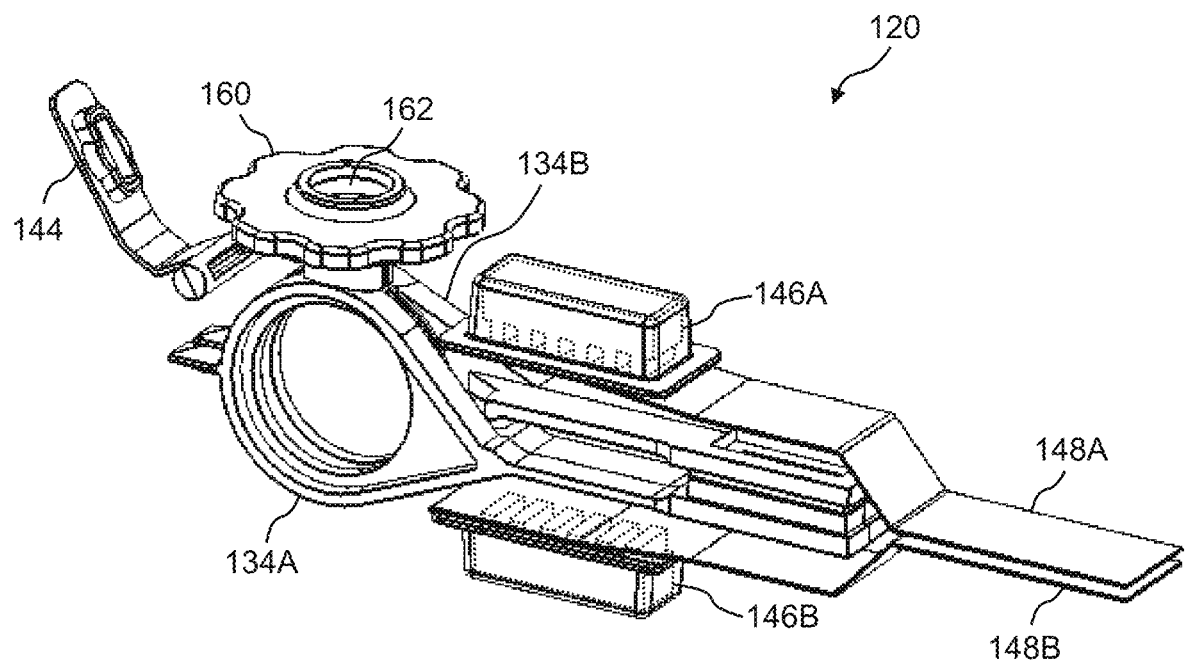
Figure 5B:
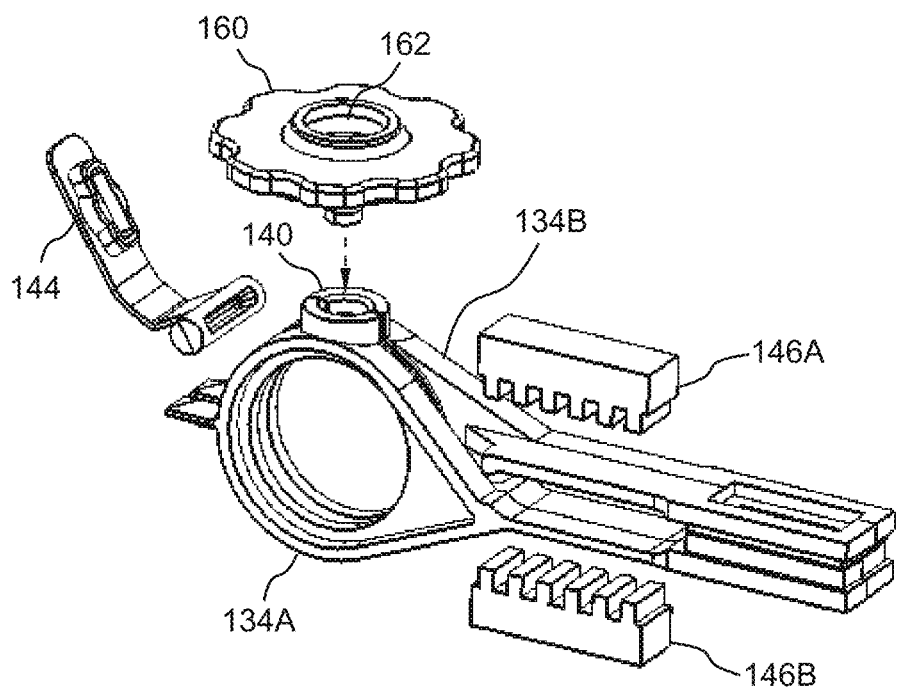
Figure 6A:
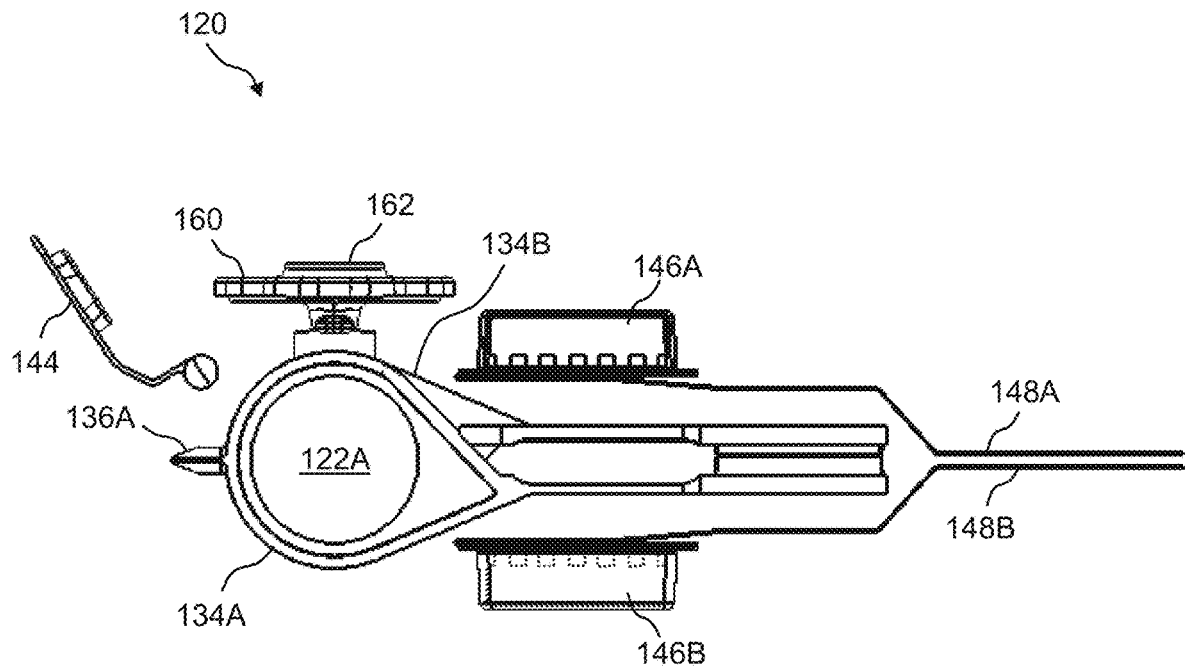
Figure 6B:
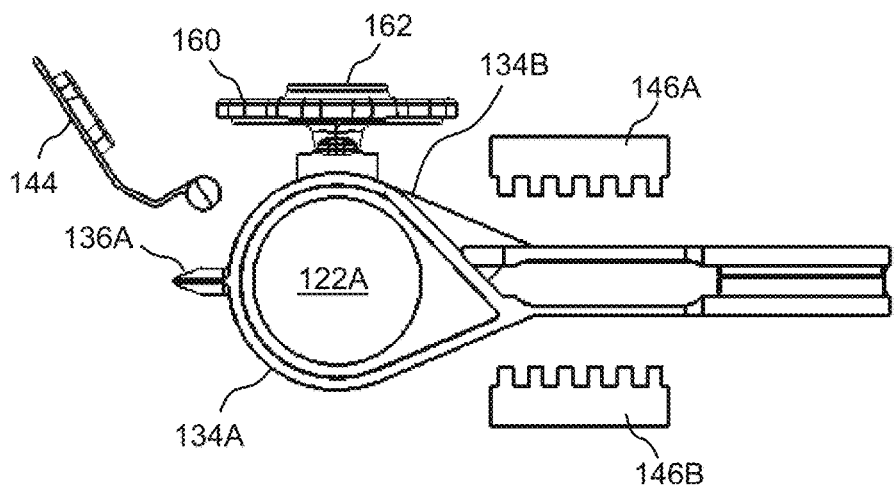
Figure 7:
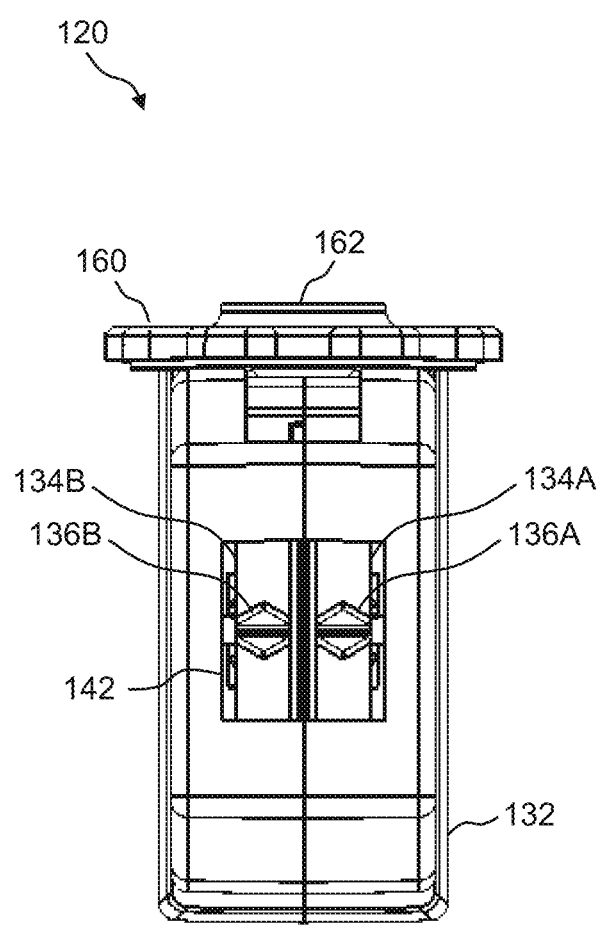
Figure 8:
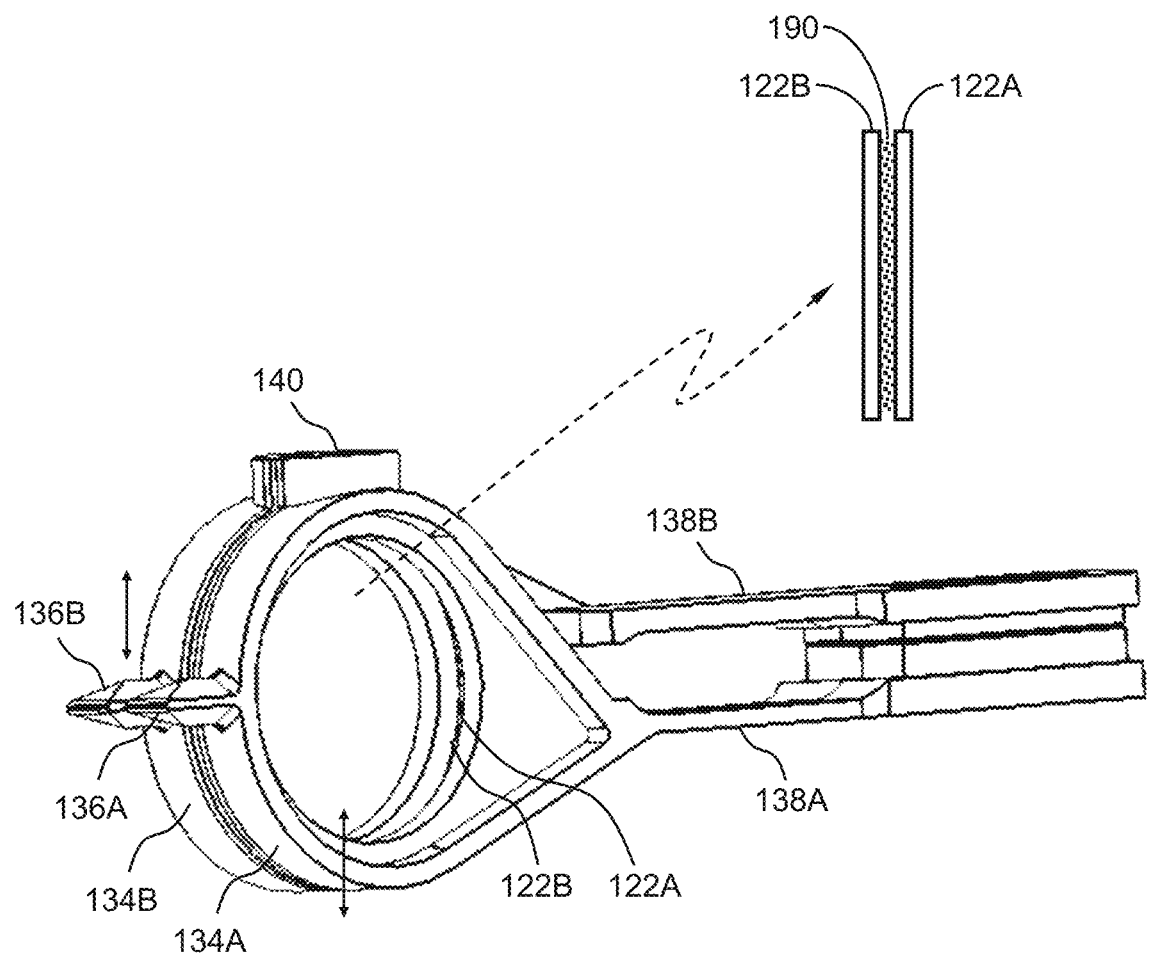
Figure 9:
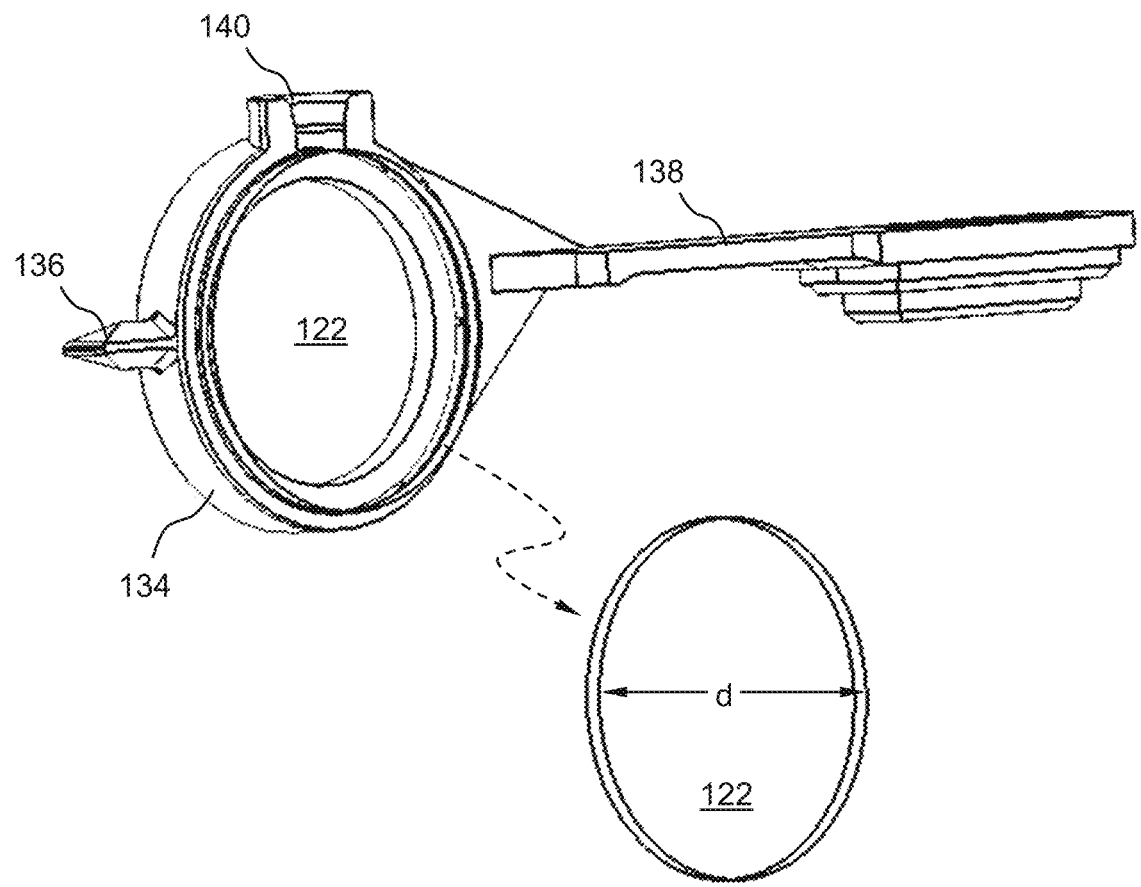
Figure 11A:
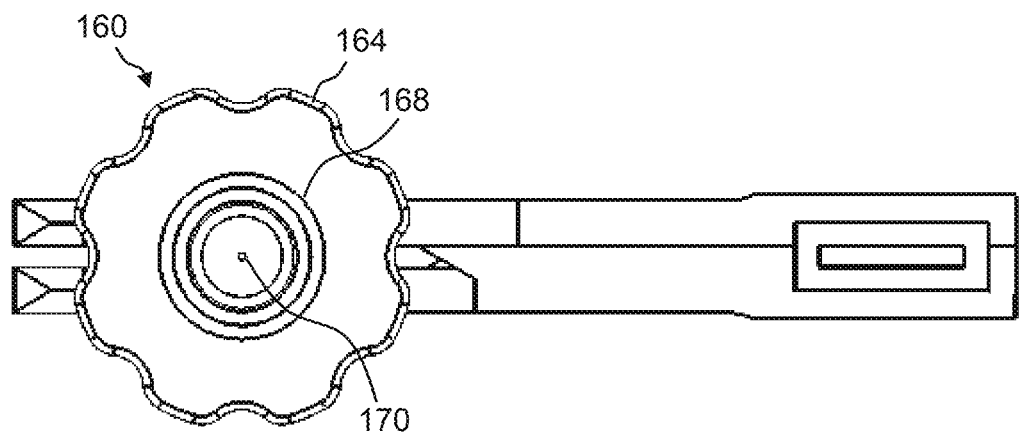
Figure 11B:
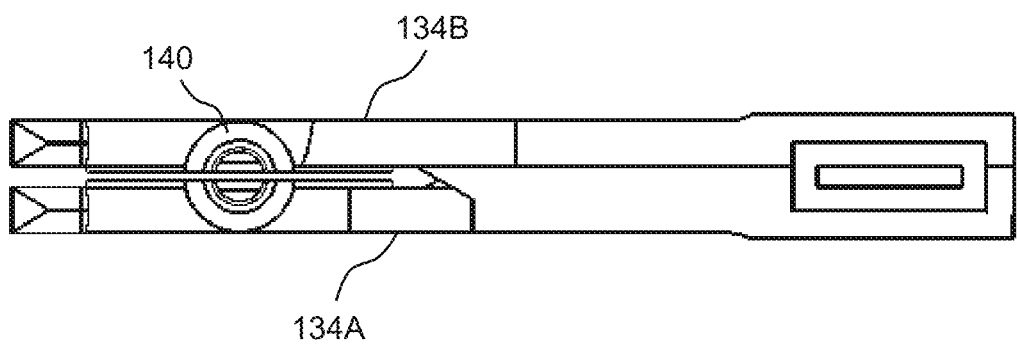
Figure 12:
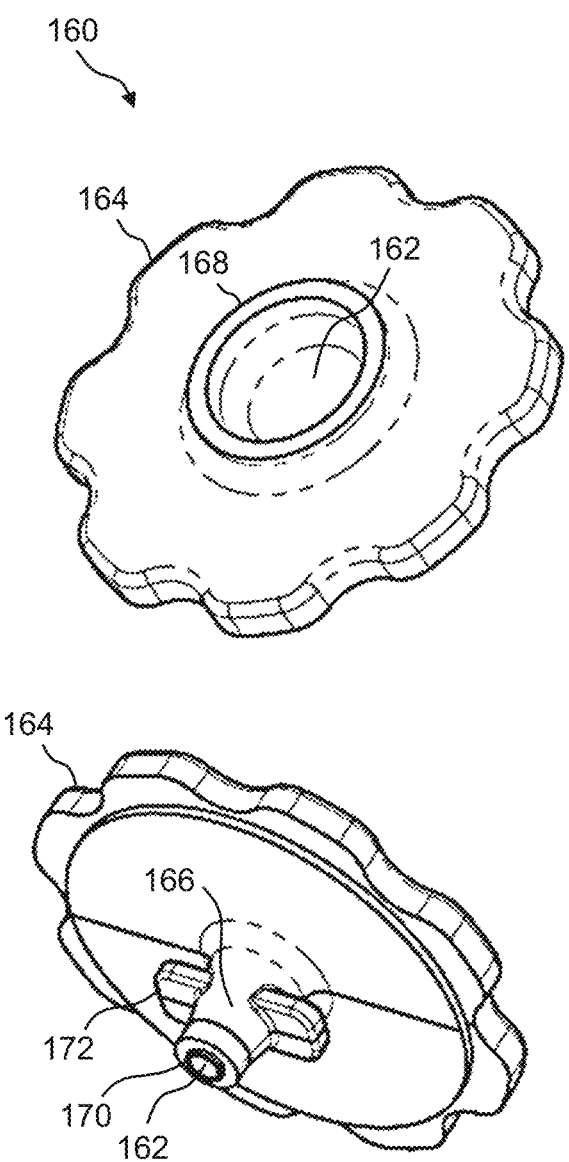
Figure 13:
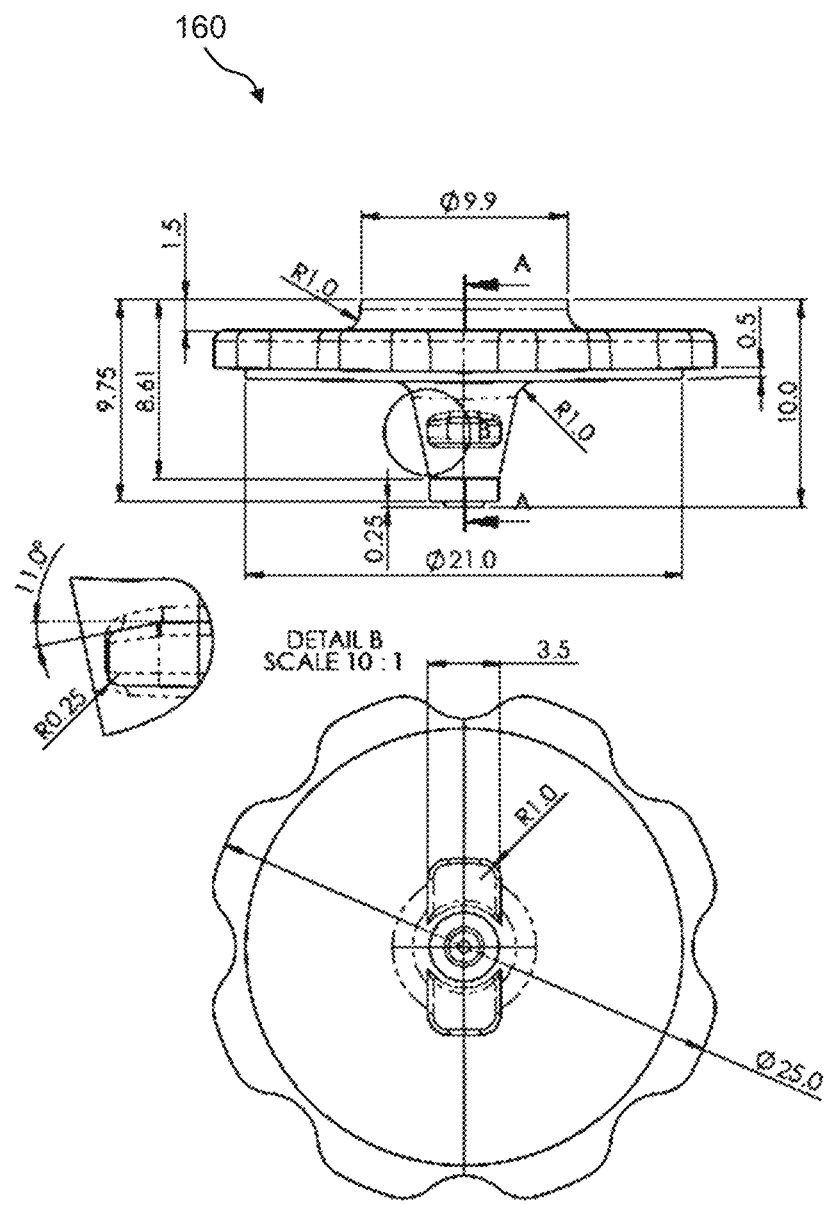
Figure 14:
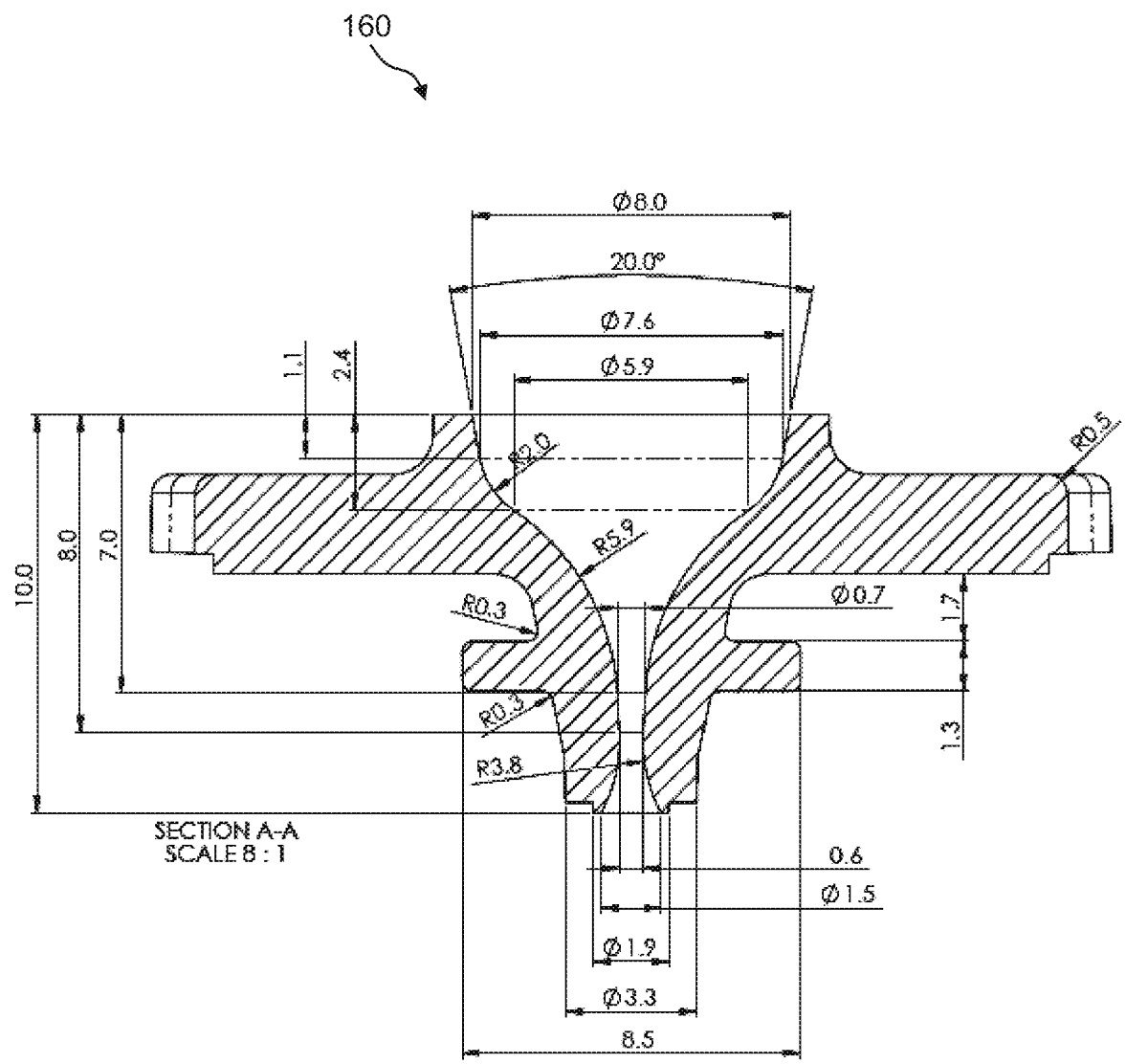
Figure 15:
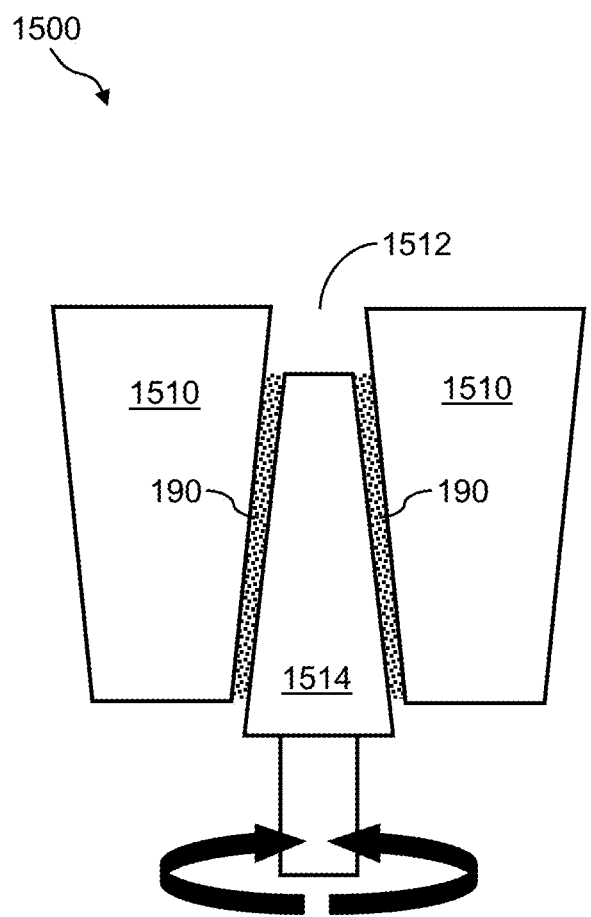
Figure 16:
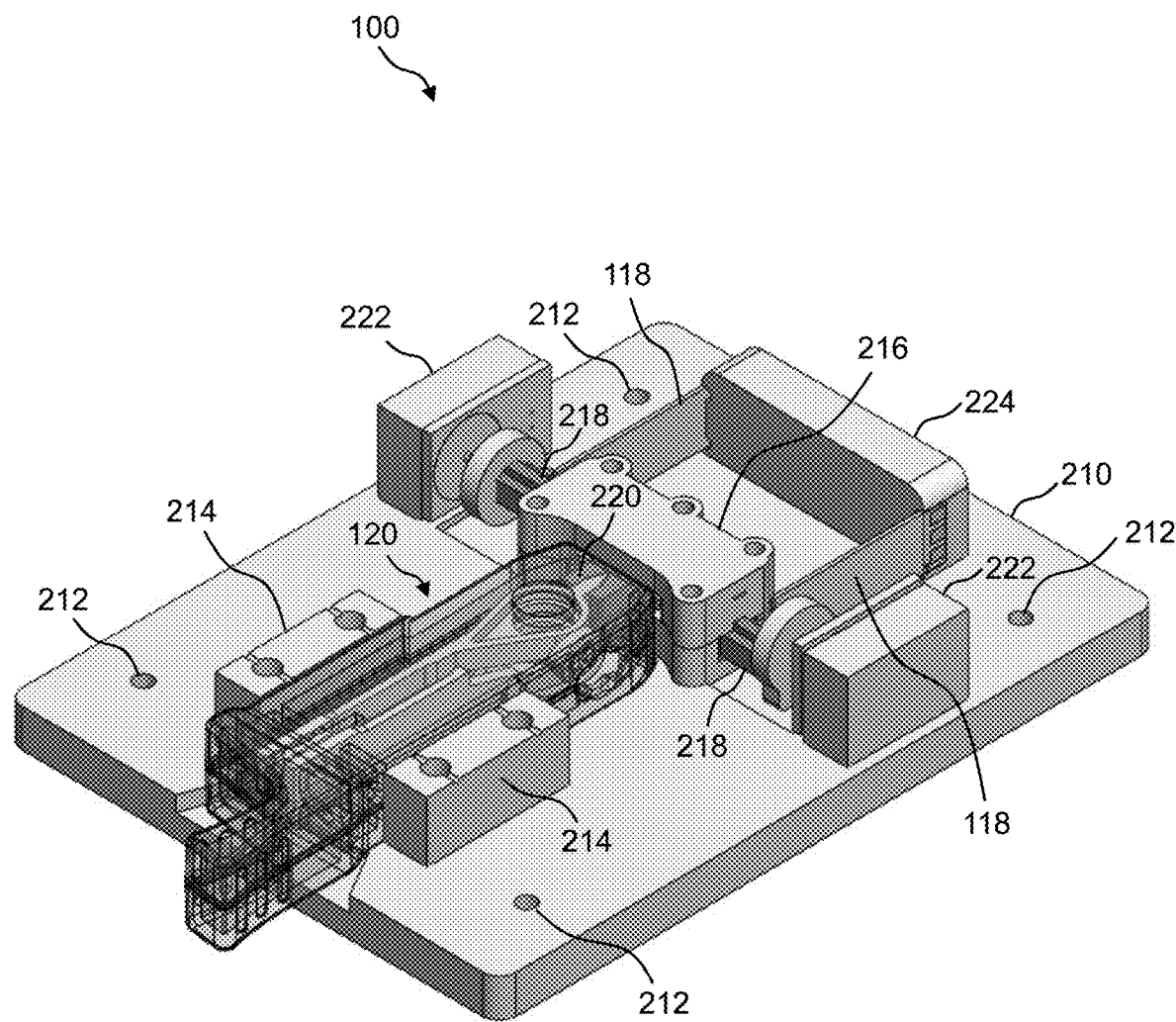
Figure 17:
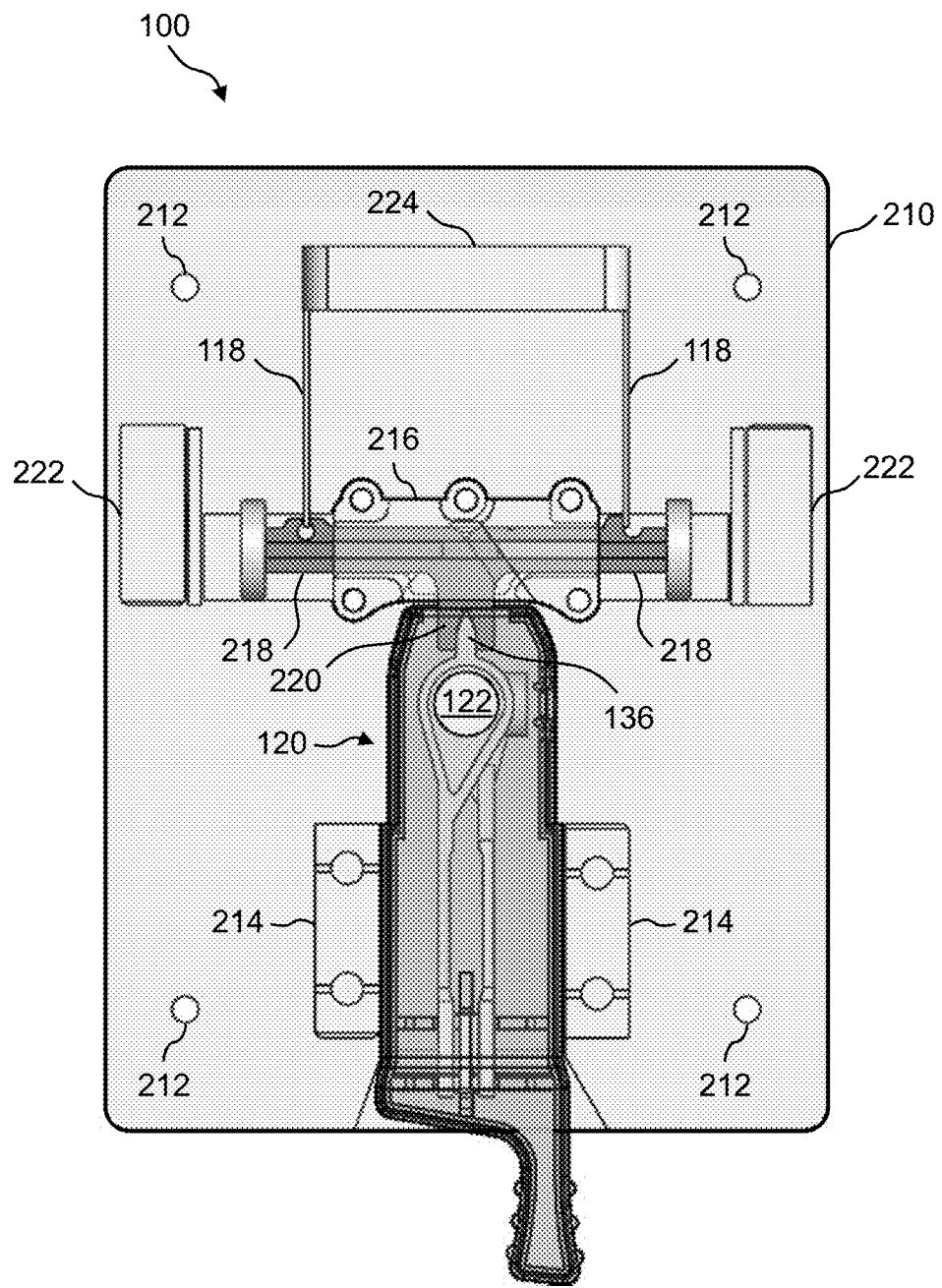
Figure 18:
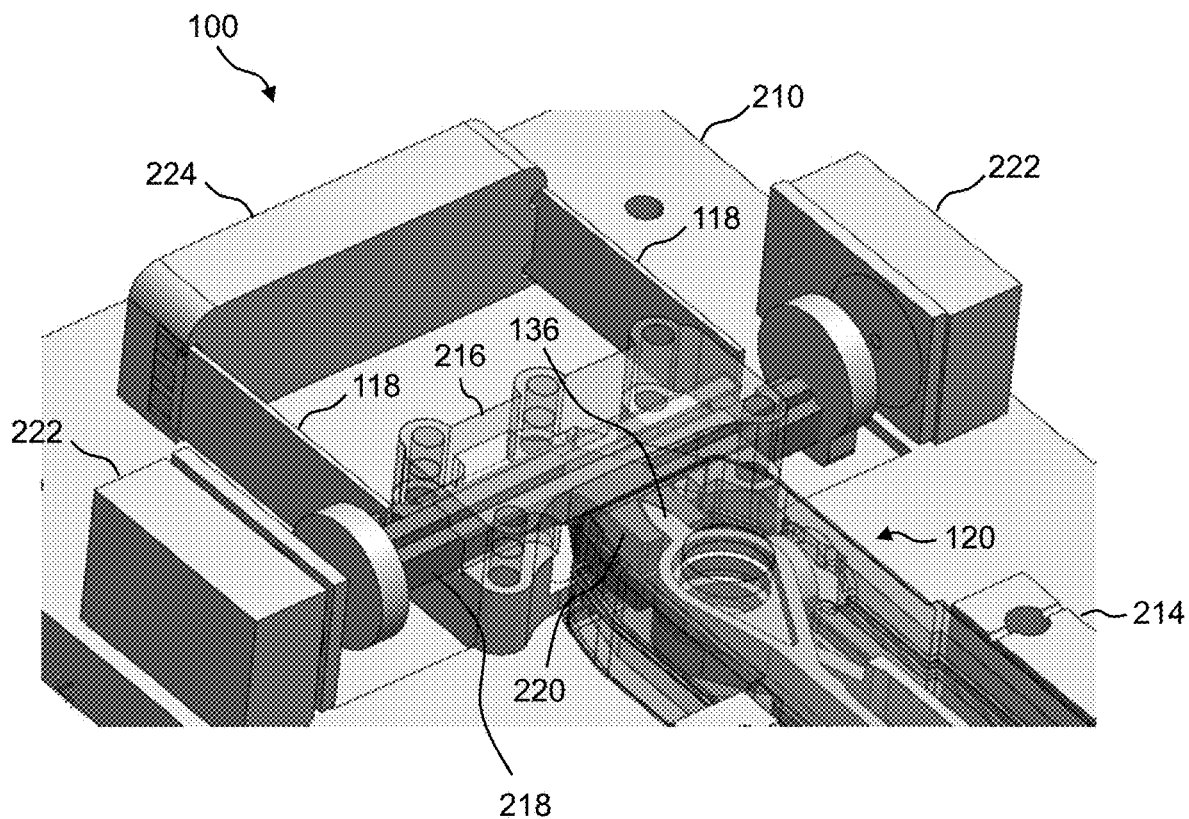
Figure 19:
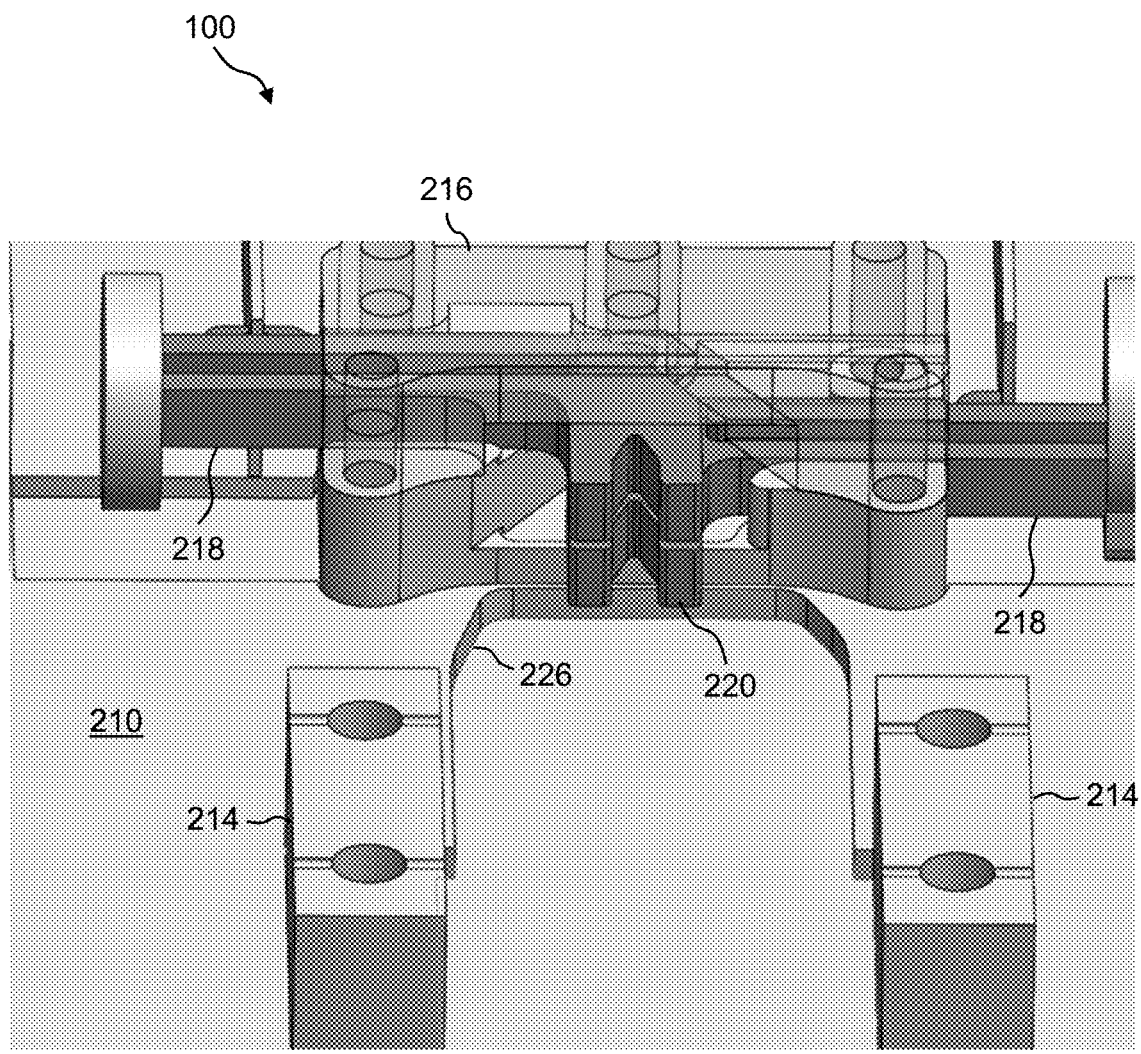
Figure 20:
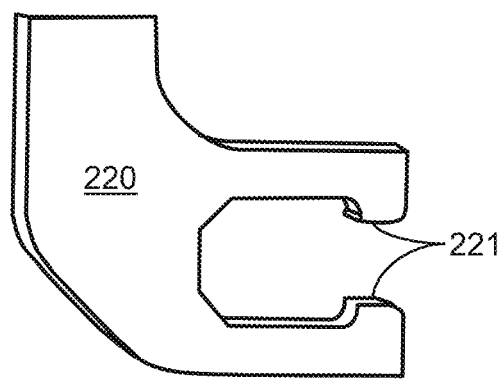
Figure 20:
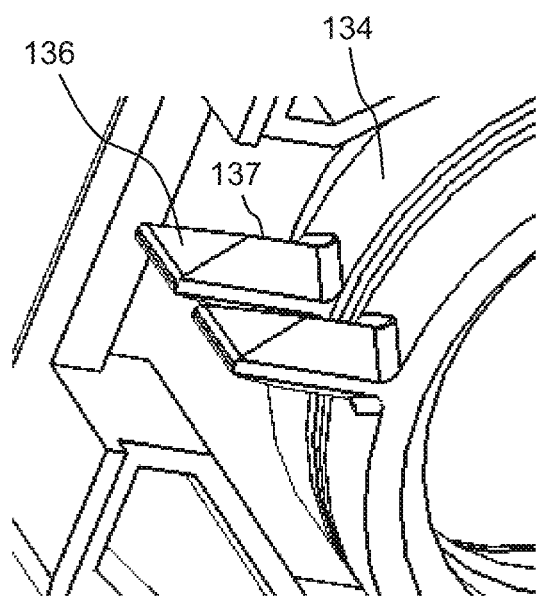
Figure 21:
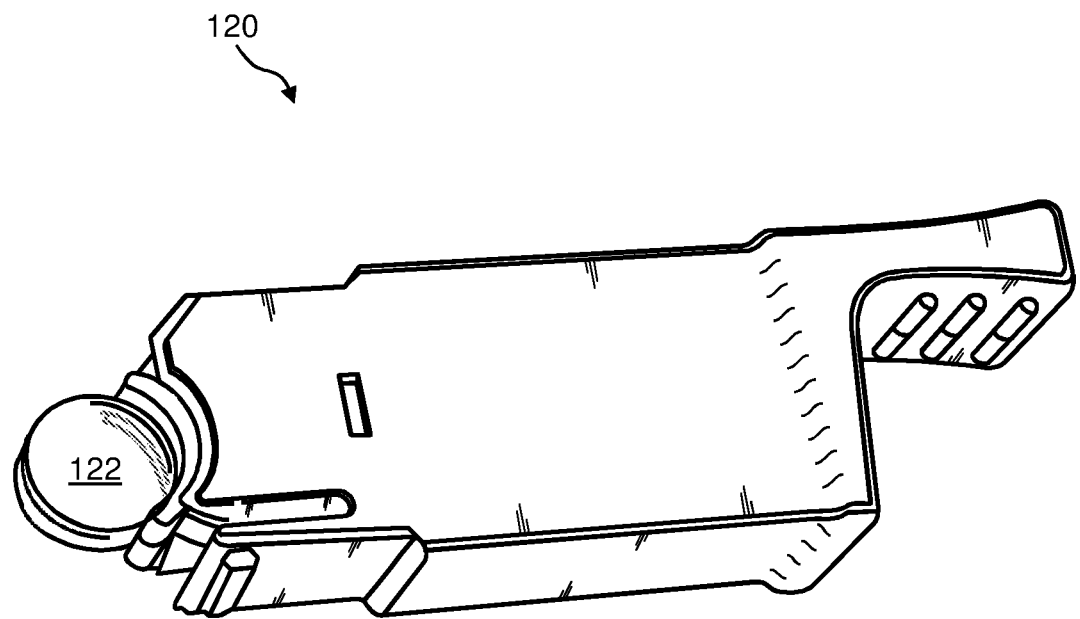
Figure 22:
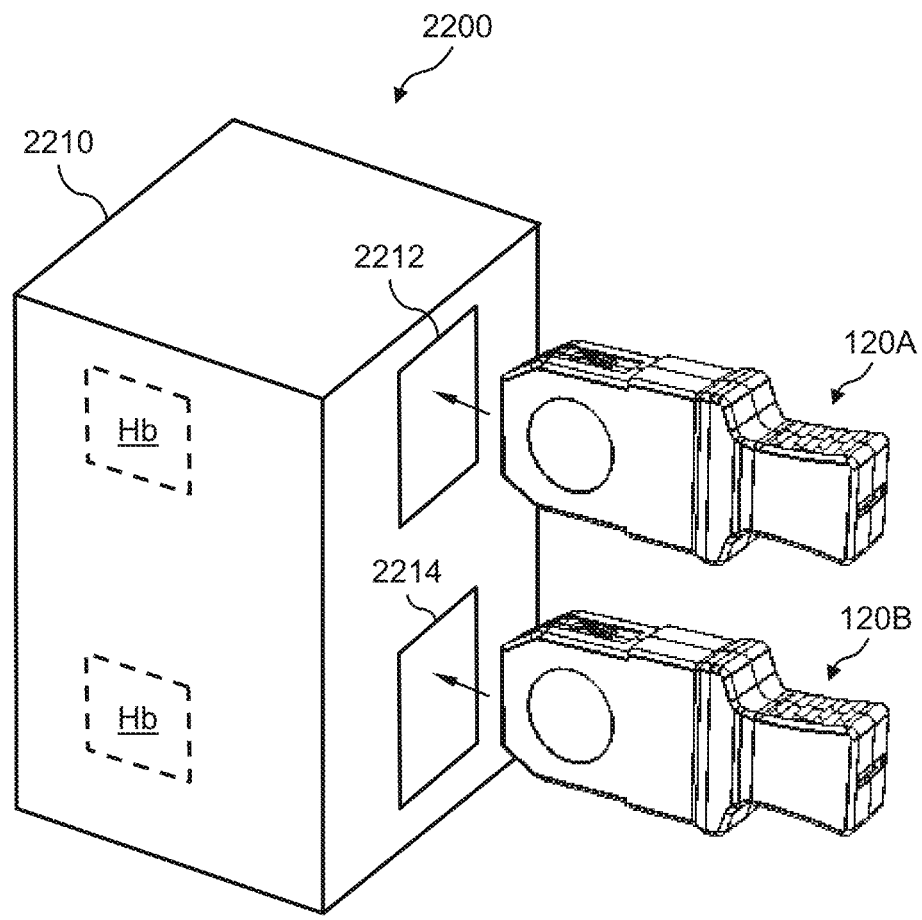
Figure 23:
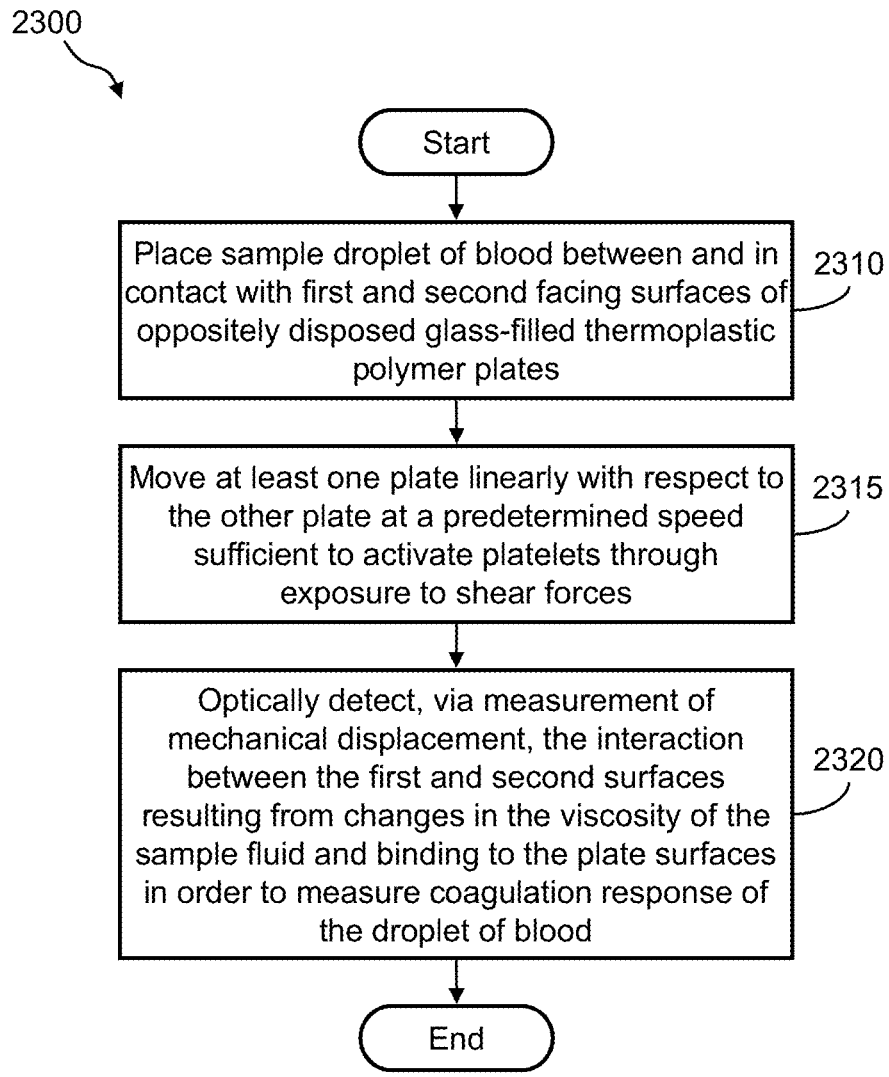
Figure 24:
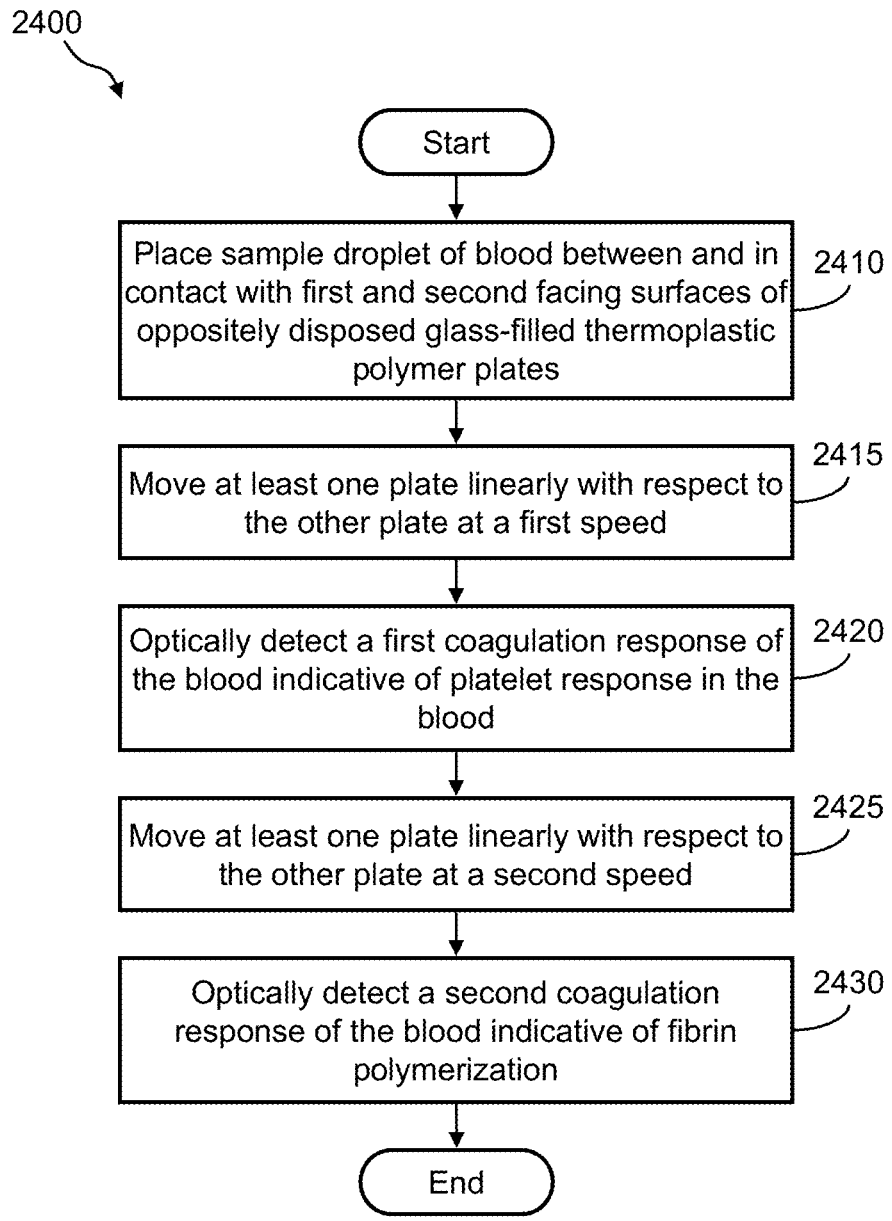
Figure 25:
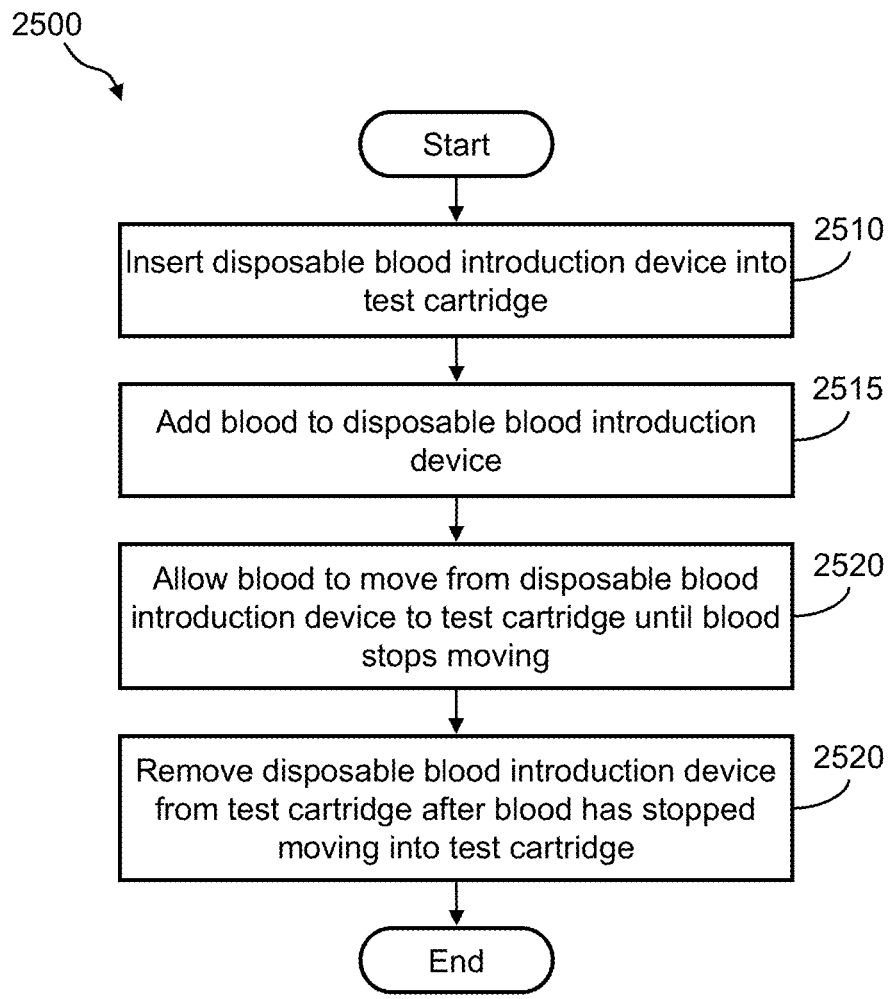

Having thus described the presently disclosed subject matter in general terms, reference will now be made to the accompanying Drawings, which are not necessarily drawn to scale, and wherein:

FIG. 1 illustrates a simplified block diagram of an example of the presently disclosed portable coagulation monitor (PCM) device comprising a test cartridge having glass-filled thermoplastic polymer plates for measurement of blood thromboelastography and a disposable blood introduction mechanism;

FIG. 2A and FIG. 2B illustrate perspective views of an example of the presently disclosed test cartridge having glass-filled thermoplastic polymer plates for measurement of blood thromboelastography and a disposable blood introduction mechanism;

FIG. 3A and FIG. 3B illustrate perspective views of the presently disclosed test cartridge with a portion of the housing removed and thereby revealing the internal components thereof;

FIG. 4A and FIG. 4B illustrate side views of the presently disclosed test cartridge with a portion of the housing removed and thereby revealing the internal components thereof;

FIG. 5A and FIG. 5B illustrate other perspective views of the presently disclosed test cartridge;

FIG. 6A and FIG. 6B illustrate side views of the presently disclosed test cartridge with the housing entirely removed and showing only the internal components thereof;

FIG. 7 illustrates an end view of the presently disclosed test cartridge when fully assembled;

FIG. 8 illustrates a perspective view of a pair of glass-filled thermoplastic polymer plates of the presently disclosed test cartridge;

FIG. 9 illustrates a perspective view of one of the glass-filled thermoplastic polymer plates of the presently disclosed test cartridge;

FIG. 10A and FIG. 10B illustrate end views of the plate carriers in relation to a disposable blood introduction mechanism of the presently disclosed test cartridge;

FIG. 11A and FIG. 11B illustrate top down views of the plate carriers with and without the disposable blood introduction mechanism of the presently disclosed test cartridge;

FIG. 12, FIG. 13, and FIG. 14 show various detailed drawings of an example of the disposable blood introduction mechanism of the presently disclosed test cartridge;

FIG. 15 illustrates a side view of an example of a glass-filled thermoplastic polymer rotation mechanism that can be used in place of the glass-filled thermoplastic polymer plates in the presently disclosed test cartridge and/or PCM device;

FIG. 16 and FIG. 17 illustrate a perspective view and a plan view, respectively, of an example of the physical instantiation of the PCM device when holding the test cartridge;

FIG. 18 illustrates a perspective view of a portion of the PCM device shown in FIG. 16 and FIG. 17;

FIG. 19 illustrates a perspective view of a portion of the PCM device shown in FIG. 16 and FIG. 17, but absent the test cartridge;

FIG. 20 illustrates an example of the actuator engagement mechanisms of the PCM device shown in FIG. 16 and FIG. 17;

FIG. 21 illustrates a perspective view of another example of a test cartridge;

FIG. 22 illustrates a perspective view of an example of a dual channel PCM device for receiving and holding two test cartridges;

FIG. 23 illustrates a flow diagram of an example of a method of measuring coagulation response in a blood sample using the presently disclosed PCM device and/or test cartridge;

FIG. 24 illustrates a flow diagram of another example of a method of measuring coagulation response in a blood sample using the presently disclosed PCM device and/or test cartridge; and FIG. 25 illustrates a flow diagram of an example of a method of introducing blood into a test cartridge using the presently disclosed disposable blood introduction device.

DETAILED DESCRIPTION

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides portable coagulation monitoring devices, systems, and methods. Namely, the presently disclosed subject matter provides a test cartridge for use in a portable coagulation monitor (PCM) or assay device, wherein the PCM device is for the diagnosis of trauma or other related coagulopathies in which it is important to assess coagulation response to optimize treatment, for example, in critical field situations wherein the first hour is critical in terms of preventing long-term debilitating events or even death.

The presently disclosed test cartridge is typically used in thromboelastigraphy (TEG) and includes, in some embodiments, two plates arranged substantially in parallel with a small gap therebetween for receiving a sample of blood to be tested. The detection of coagulation may be done, for example, optically by measuring mechanical interaction between the surfaces of the two plates resulting from changes in the viscosity of the sample fluid and binding of the sample fluid to the plate surfaces. In one example, the two plates are glass-filled thermoplastic polymer plates in which the surfaces face each other, and are spaced an amount sufficient to allow a relatively small sample of blood to contact the facing surfaces of the two plates at the same time without an air space between. The glass-filled thermoplastic polymer plates may then be agitated to induce the platelet clotting process for measurement of blood thromboelastigraphy.

Further, the presently disclosed test cartridge may include a disposable blood introduction device to dose the correct amount of blood into the test cartridge using capillary action, without the need to measure the blood. The disposable blood introduction device may be used to fill the test cartridge with the correct amount of blood and any extra blood in the device may then be safely disposed of with the device. The disposable blood introduction device typically includes a funnel or the like for introduction of the blood into the test cartridge and an outlet to allow blood to move from the funnel into the test cartridge.

Referring now to FIG. 1, a simplified block diagram is shown depicting an example of the presently disclosed portable coagulation monitor (PCM) device 100 that includes a test cartridge, wherein the test cartridge includes glass-filled thermoplastic polymer plates for measurement of blood thromboelastigraphy and a disposable blood introduction device.

PCM device 100 may be used for the diagnosis of trauma or other related coagulopathies in which it is important to assess coagulation response to optimize treatment, for example, in critical field situations wherein the first hour is critical in terms of preventing long-term debilitating events or even death. In one example, PCM device 100 is based on the PCM device described with reference to U.S. Pat. No. 8,450,078, entitled "Portable Coagulation Monitoring Device and Method of Assessing Coagulation Response," the entire disclosure of which is incorporated herein by reference ("the '078 patent"). The '078 patent describes a device, system and method in which small-volume blood samples may be subjected to shear forces and shear stresses between two parallel planar surfaces to which linear motion trajectories are imparted. The formation of clots or coagulation of the sample is measured from dynamic mechanical coupling which occurs between the two parallel planar surfaces. Detection of the coagulation response can be achieved through optical probing or by measurement of physical effects of the blood sample binding to the planar surfaces, and restricting movement thereof.

In this example, PCM device 100 may include one or more of a power source 106, a controller 108, a communications interface 110, a user interface 112, an optics system 114, a temperature control mechanism 116, and a pair of actuators 118 (e.g., actuators 118A, 118B). Those skilled in the art will recognize that PCM device 100 may include other components, which are not shown, such as, but not limited to, any types of motors, any types of sensors, any types of device-specific drivers and/or controllers, data storage (i.e., volatile and/or nonvolatile memory), and the like.

Further, PCM device 100 can be ruggedized to allow for use during impacts and/or vibrations. In one example, PCM device 100 may include an internal accelerometer (not shown) that can be used to measure such impacts and/or vibrations and allow PCM device 100 to compensate accordingly. PCM device 100 may also be designed to be versatile and measure platelet and fibrin clotting over a wide dynamic range of shear. Additionally, PCM device 100 can operate on USB hub power as a peripheral device with components that are readily manufactured and assembled.

PCM device 100 may also include mechanical features (not shown) for receiving and holding a test cartridge 120, for example, a TEG test cartridge. Namely, test cartridge 120 may be a pluggable component of PCM device 100, as shown in FIG. 1. Together, PCM device 100 and test cartridge 120 may be considered a PCM system. More details of an example of the physical instantiation of PCM device 100 for receiving and holding test cartridge 120 are shown and described hereinbelow with reference to FIG. 16 through FIG. 20.

Power source 106 can be, for example, any rechargeable or non-rechargeable battery. In one example, power source 106 is a 3.7-volt battery, rated at about 96 mA and with a battery life of about 4 hours. In certain other embodiments, power source 106 may be external to the PCM device 100, or may include any suitable internal or external power source.

Controller 108 can be any standard controller or microprocessor device that is capable of executing program instructions. Controller 108 can be used to manage the overall operations of PCM device 100 including those of communications interface 110, user interface 112, optics system 114, temperature control mechanism 116, and actuators 118.

Communications interface 110 may be any wired and/or wireless communication interface for connecting to a network (not shown) and by which information may be exchanged with other devices connected to the network. Examples of wired communication interfaces may include, but are not limited to, USB ports, RS232 connectors, RJ45 connectors, Ethernet, and any combinations thereof. Examples of wireless communication interfaces may include, but are not limited to, an Intranet connection, Internet, ISM, Bluetooth® technology, Bluetooth® Low Energy (BLE) technology, Wi-Fi, Wi-Max, IEEE 402.11 technology, ZigBee technology, Z-Wave technology, 6LoW-PAN technology (i.e., IPv6 over Low Power Wireless Area Network (6LoWPAN)), ANT or ANT+ (Advanced Network Tools) technology, radio frequency (RF), Infrared Data Association (IrDA) compatible protocols, Local Area Networks (LAN), Wide Area Networks (WAN), Shared Wireless Access Protocol (SWAP), any combinations thereof, and other types of wireless networking protocols.

User interface 112 can include any pushbutton controls, video display, touchscreen display, and/or any other types of visual, audible, and/or tactile indicators.

Optics system 114 can include, for example, a laser or other light source in combination with one or more optical detectors (or light sensors).

Temperature control mechanism 116 can be any mechanism for maintaining test cartridge 120 at a desired temperature (e.g., about 38° C.) during use. Temperature control mechanism 116 can be, for example, a peltier cooler or resistive heater. A heater controller and various feedback mechanisms (e.g., negative temperature coefficient (NTC) thermistor, a thermocouple device, and the like) may be associated with temperature control mechanism 116. Note further that the temperature control mechanism 116 may be included either within the PCM device 100 or within the test cartridge 120.

Actuators 118 (e.g., actuators 118A, 118B) can be, for example, based on Piezo technology. In one example, actuators 118 are Piezo motors coupled to flexing ceramic actuators (see FIG. 16, FIG. 17, FIG. 18) having, for example, a displacement to about 2 mm, fast response in the millisecond range, nanometer resolution, and a low operating voltage. In one example, actuators 118 are capable of delivering mechanical shear to the blood sample over a wide dynamic range of mechanical oscillations of from about 0.0001 Hz to about 1000 Hz. In certain other embodiments, actuators 188 may include voice coil motors, or any other motor suitable for use in PCM device 100.

Test cartridge 120 may include two glass-filled thermoplastic polymer plates 122 (e.g., glass-filled thermoplastic polymer plates 122A, 122B) arranged substantially in parallel with each other and with a small gap therebetween for receiving a sample of blood to be tested. The surfaces of glass-filled thermoplastic polymer plates 122A, 122B face each other, and are spaced an amount sufficient to allow a relatively small sample of blood to contact the facing surfaces of glass-filled thermoplastic polymer plates 122A, 122B at the same time without an air space between.

In some embodiments, actuator 118A is mechanically coupled to glass-filled thermoplastic polymer plate 122A and actuator 118B is mechanically coupled to glass-filled thermoplastic polymer plate 122B. Using actuators 118A, 118B of PCM device 100, glass-filled thermoplastic polymer plates 122A, 122B can be agitated to induce the platelet clotting process for measurement of blood thromboelastigraphy. Namely, using actuators 118A, 118B, glass-filled thermoplastic polymer plates 122A, 122B are movable relative to each other in a parallel and linear direction, and the spacing is such that the components of blood can initiate coagulation or adherence to each of the surfaces.

In test cartridge 120, the small gap between glass-filled thermoplastic polymer plates 122A, 122B can be, for example, from about 50 µm to about 250 µm. Using actuators 118A, 118B of PCM device 100, glass-filled thermoplastic polymer plates 122A, 122B slide past each other with controlled velocity to create a shear stress between the plates which is represented as $T=\mu V/D$ where T equals shear stress, $\mu$=viscosity, $V=V1+V2$, wherein V is equal to the relative linear velocity of the plates, and D=gap between the plates.

Using optics system 114, the coagulation response can be detected. Namely, optics system 114 may be used for detecting interaction of light with a blood sample located between glass-filled thermoplastic polymer plates 122A, 122B, with the interaction of light and detection thereof providing an indication of coagulation response of the blood sample. More specifically, with appropriate positioning of a light source and detectors (not shown), over time and in accordance with the variation of the movement of the glass-filled thermoplastic polymer plates 122A, 122B to generate a particular shear rate, information about both platelet response, fibrin response, and other responses of the blood components during coagulation can be obtained.

Using optics system 114, optical detection may be done by transmitting light into the sample droplet, and detecting at least one of transmission, reflection and refraction of the light through the sample droplet at respective light detectors. Analog signals may be generated from the detection at the light detectors representative of coagulation properties of the blood in the sample droplet. Glass-filled thermoplastic polymer plates 122A, 122B are plates that are suitably transparent to allow light transmission of about 90% or more of the incident light intensity. Namely, glass-filled thermoplastic polymer plates 122A, 122B are substantially optically transparent to allow optical signals to pass through the blood sample allowing direct optical visualization of a portion or all of the blood sample between the planar surfaces of glass-filled thermoplastic polymer plates 122A, 122B. This allows transmission, reflection, internal reflection, selective absorption, polarization or optical rotation, frustrated internal reflection (either partial or total), and conduction of laser beams or other light sources.

In optics system 114, optical sensors are provided in position relative to glass-filled thermoplastic polymer plates 122A, 122B of test cartridge 120 for detecting light being projected from, for example, a laser or other light source (not shown), through and into a sample between glass-filled thermoplastic polymer plates 122A, 122B. The light can then be detected as light transmitted through the sample, reflected, refracted or otherwise modified in the path through the sample, and detected by optical sensors to obtain information about the coagulation properties of the blood sample.

More specifically, PCM device 100 and test cartridge 120 allow for the measurement of coagulation response based on the knowledge that the biophysical response of blood depends in part on the relative shear rate between the blood and surfaces with which it is in contact. More specifically, the higher the shear rate, the greater the platelet response so that the platelets then stick to the surfaces of the plates, and thereby trigger the fibrin polymerization and couple the motion of the two plates when only one is driven by the actuators (e.g., 118A, 118B). More specifically, it is recognized that in hemorrhaging events platelets need to react quickly so the use of a high shear rate for a short time period can allow accurate assessment of platelet response for these conditions. Thereafter, lower shear rates can be employed in terms of relative movements of the plates or members with respect to each other, to obtain an accurate assessment of fibrin response, or at an intermediate shear rate, both fibrin and platelet response.

"Shear" here is defined as the acceleration force felt by a particle in the moving bulk flow of fluid (blood) at the interface with the stationary solid (face of the glass plates). The shear "rate" is the differential of velocities felt on different aspects of the particle's cross-sectional area and is dependent on the particle's distance from the stationary surface.

Test cartridge 120 may further include a humidity control mechanism 124. Humidity control mechanism 124 may be used to keep the inside of test cartridge 120 relatively moist, thereby slowing the drying time of the blood sample between glass-filled thermoplastic polymer plates 122A, 122B. In one example, humidity control mechanism 124 is one or more sponge-like pads that are placed inside test cartridge 120, wherein the sponge-like pads are wetted, placed inside one or more sealed humidity pouches, and then installed in test cartridge 120. A user may then optionally open the humidity pouches to slow drying of the blood sample. Examples of the sponge-like pads are shown hereinbelow with reference to FIG. 3A through FIG. 7.

Test cartridge 120 may further include a disposable blood introduction device 160. Disposable blood introduction device 160 is used to dose the correct amount of blood into test cartridge 120 using capillary action, without the need for a user to measure the blood. Disposable blood introduction device 160 may be used to fill test cartridge 120 with the correct amount of blood. Any extra blood in disposable blood introduction device 160 may then be safely disposed of together with disposable blood introduction device 160. Disposable blood introduction device 160 typically includes a funnel or the like for introduction of the blood therein and a capillary at a flat bottom thereof that allows blood to move from disposable blood introduction device 160 into test cartridge 120. More details of an example of test cartridge 120 are shown and described hereinbelow with reference to FIG. 2A through FIG. 14, with specific details of disposable blood introduction device 160 shown in FIG. 12, FIG. 13, and FIG. 14.

Referring now to FIG. 2A through FIG. 7, various views are shown of an example of the presently disclosed test cartridge 120 having glass-filled thermoplastic polymer plates 122 for measurement of blood thromboelastography and having disposable blood introduction device 160. Namely, FIG. 2A and FIG. 2B are perspective views of test cartridge 120 when fully assembled; FIG. 3A and FIG. 3B are perspective views and FIG. 4A and FIG. 4B are side views of test cartridge 120 with a portion of the housing removed and thereby revealing the internal components thereof; FIG. 5A and FIG. 5B are perspective views and FIG. 6A and FIG. 6B are side views of test cartridge 120 without the housing thereof; and FIG. 7 is an end view of test cartridge 120 when assembled.

Referring now to FIG. 2A and FIG. 2B, test cartridge 120 comprises a housing 132 for holding all the components thereof. In one example, housing 132 may be a two-piece housing, wherein the two pieces are snap-fitted or adhered together. Housing 132 can be formed, for example, of molded plastic. One end of housing 132 can have a grip-like shape, while the opposite end of housing 132 can have an opening 142 through which glass-filled thermoplastic polymer plates 122A, 122B can be engaged with actuators 118A, 118B of PCM device 100, which are typically external to test cartridge 120. Housing 132 may also have an optics window 150 in each side of housing 132. The optics windows 150 substantially align with glass-filled thermoplastic polymer plates 122A, 122B and are used by optics system 114 of PCM device 100 for transmitting light in and out of test cartridge 120.

FIG. 2A and FIG. 2B also show disposable blood introduction device 160 snap-fitted or press-fitted into housing 132 of test cartridge 120. Disposable blood introduction device 160 may include a fluid channel 162 that is fluidly coupled to a fluid channel between glass-filled thermoplastic polymer plates 122A, 122B (see FIG. 10A and FIG. 10B). A cap 144 may also be provided for closing the opening that corresponds to disposable blood introduction device 160 when disposable blood introduction device 160 is not present in test cartridge 120. Cap 144 can be, for example, pivotably coupled to housing 132.

Referring now to FIG. 3A through FIG. 7, test cartridge 120 may further include a pair of movable plate carriers 134 for holding glass-filled thermoplastic polymer plates 122. For example, test cartridge 120 may include plate carrier 134A for holding glass-filled thermoplastic polymer plate 122A and plate carrier 134B for holding glass-filled thermoplastic polymer plate 122B. Each plate carrier 134 can be a flexible elongated member (e.g., a thermoplastic member). One end of the elongated member can be held stationary in housing 132 and the other end can include a frame for holding glass-filled thermoplastic polymer plate 122, wherein the frame portion of each plate carrier 134 is substantially floating in midair. Accordingly, the frame portion of plate carrier 134 that is holding glass-filled thermoplastic polymer plate 122 may be movable. More particularly, the frame portion of plate carrier 134A may be movable in a parallel and linear direction with respect to the frame portion of plate carrier 134B.

Additionally, the frame portion of plate carrier 134 may include an engagement feature 136. Namely, plate carrier 134A may include engagement feature 136A and plate carrier 134B may include engagement feature 136B (see FIG. 7). Engagement features 136A, 136B are accessible through opening 142 of housing 132 and can be mechanically engaged with actuators 118A, 118B of PCM device 100.

The frame portion of plate carrier 134 is typically shaped according to the shape of glass-filled thermoplastic polymer plate 122. In one example, glass-filled thermoplastic polymer plate 122 is a circular disc. However, glass-filled thermoplastic polymer plate 122 and accordingly the frame portion of plate carrier 134 can be any shape, such as circular, ovular, square, rectangular, triangular, polygonal, and the like.

Referring still to FIG. 3A through FIG. 6B, test cartridge 120 may also include a pair of humidity pads 146 (e.g., humidity pads 146A, 146B). Humidity pads 146A, 146B are one example of humidity control mechanism 124 of test cartridge 120 as described in FIG. 1. For example, humidity pads 146A, 146B may be sponge-like pads that are placed inside test cartridge 120, wherein the sponge-like pads are wetted and then installed in test cartridge 120. Humidity pads 146A, 146B are used to keep the inside of test cartridge 120 relatively moist and to slow the drying time of the blood sample between glass-filled thermoplastic polymer plates 122A, 122B. Test cartridge 120 is not limited to two humidity pads 146. Test cartridge 120 can include any number of humidity pads 146.

In some embodiments, each of the humidity pads 146 may be provided in a humidity pouch that is sealed, for example, using a foil seal for storage, but that can be peeled away when test cartridge 120 is ready for use. Accordingly, a pull tab 148 can be provided with each humidity pad 146 for pulling away the foil seal and exposing humidity pad 146. In the exemplary embodiment shown in, e.g., FIG. 3A and FIG. 3B, humidity pad 146A has a pull tab 148A and humidity pad 146B has a pull tab 148B. FIG. 4A, FIG. 4B, and FIG. 5B, and FIG. 6B show test cartridge 120 with pull tabs 148A, 148B removed and humidity pads 146A, 146B exposed.

With each test using test cartridge 120, a certain disposable blood introduction device 160 may be installed and the blood sample introduced into the gap between glass-filled thermoplastic polymer plates 122A, 122B. Upon completing the blood introduction between glass-filled thermoplastic polymer plates 122A, 122B the disposable blood introduction device 160 may be removed and cap 144 secured. For example, FIG. 4A shows disposable blood introduction device 160 installed in test cartridge 120, whereas FIG. 4B shows disposable blood introduction device 160 not installed in test cartridge 120 and cap 144 secured.

Further, FIG. 5B shows the process of fitting disposable blood introduction device 160 into a blood introduction channel 140 formed by the arrangement of plate carriers 134A, 134B. Namely, an outlet of disposable blood introduction device 160 may be press-fitted or snap-fitted into blood introduction channel 140, then blood may flow from fluid channel 162 of disposable blood introduction device 160 into blood introduction channel 140, and then into the gap between glass-filled thermoplastic polymer plates 122A, 122B.

Referring now to FIG. 8, which is a perspective view of a pair of glass-filled thermoplastic polymer plates 122, and FIG. 9 which is a perspective view of one glass-filled thermoplastic polymer plate 122, each plate carrier 134 may include a flexing portion 138. Plate carriers 134A, 134B are designed and positioned to hold the planar glass-filled thermoplastic polymer plates 122A, 122B substantially parallel and with a small gap in between for holding, for example, a blood sample 190. Namely, the frame portion of plate carrier 134A is movable in a parallel and linear direction with respect to the frame portion of plate carrier 134B. The spacing of glass-filled thermoplastic polymer plates 122A, 122B in plate carriers 134A, 134B is such that the components of blood can initiate coagulation or adherence to each of the surfaces. For example, the small gap between glass-filled thermoplastic polymer plates 122A, 122B can be, for example, from about 50 μm to about 250 μm.

Further, the shape of engagement features 136 is designed to inhibit spreading when in use. Additionally, in one example, each glass-filled thermoplastic polymer plate 122 has a diameter d of about 20 mm (see FIG. 9).

The glass constituent in glass-filled thermoplastic polymer plates 122 activates the platelets and induces blood clotting. The thermoplastic carrier (e.g., plate carriers 134) allows the test cartridge 120 design to incorporate disposable blood introduction device 160, allows custom-made shaping to maximize sensitivity and assay accuracy, minimizes the number of components in test cartridge 120, minimizes costs, and allows for numerous mechanisms of platelet activation. There is no need for multiple components or the use of whole glass discs.

The polymers used in glass-filled thermoplastic polymer plates 122 can be a variety of polymers, such as nylon (polyamide), polycarbonate, polypropylene, polyethylene and polyester. Accordingly, in some embodiments, the glass-filled thermoplastic polymer is selected from the group consisting of nylon (polyamide), polycarbonate, polypropylene, polyethylene and polyester. In some embodiments, the amount of glass within the polymer can be between about 5% to about 60%. In other embodiments, the amount of glass within the polymer is about 30%. Accordingly, in some embodiments, the glass-filled thermoplastic polymer contains glass beads and/or glass fibers and the amount of glass beads and/or glass fibers within the glass-filled thermoplastic polymer is between about 5% to about 60%. In other embodiments, the amount of glass beads and/or glass fibers within the glass-filled thermoplastic polymer is about 30%.

In some embodiments, the glass in glass-filled thermoplastic polymer plates 122 can be found as fibers, beads, irregular pieces, or any form that activates the platelets in blood and induces blood clotting. In other embodiments, glass-filled thermoplastic polymer plates 122 are injection molded. In still other embodiments, glass-filled thermoplastic polymer plates 122 can be designed with intricate three-dimensional structures, such as thin channels, capillaries, undercuts and/or holes depending on the specific applications of the device.

In further embodiments, test cartridge 120 may further include at least one structure selected from the group consisting of a channel, a capillary, an undercut, and a hole. For example, a blood introduction system that includes a capillary or channel can be fully incorporated into the design of test cartridge 120, allowing for test cartridge 120 to be used as a diagnostic test. In this example, the capillary plate and linkage arms are one single piece and therefore the capillary or channel is molded in one step. The inclusion of disposable blood introduction device 160 allows the blood of a subject to be added directly into test cartridge 120 without the need for external pipettes because the blood is delivered directly to the capillary/measurement area. Additionally, there is no need to measure or dose the blood because the correct amount of blood is delivered to the clot measurement area. In some embodiments, the glass-filled thermoplastic polymers can be used for the simultaneous introduction of blood samples and the measurement of clotting (including platelet activation and extrinsic pathways) in the measurement of blood thromboelastography. In other embodiments, the first glass-filled thermoplastic polymer plate 122A and second glass-filled thermoplastic polymer plate 122B of test cartridge 120 make up a blood sample collection cartridge which is removable from PCM device 100. In still other embodiments, PCM device 100 further includes a memory device for storing data relating to a blood sample tested.

In some embodiments, the first and/or the second surface of the glass-filled thermoplastic polymer plates 122 have been treated to induce, slow, or modify the coagulation process for selecting in favor of or against specific aspects of coagulation of the sample. In other embodiments, treatment of the surfaces of the glass-filled thermoplastic polymer plates 122 enhances at least one characteristic selected from the group consisting of platelet or blood protein binding, reactivity, and activation. In yet other embodiments, the treatment of the surfaces reduces at least one characteristic selected from the group consisting of platelet or blood protein binding, reactivity, and activation. In further embodiments, PCM device 100 and/or test cartridge 120 are configured for analyzing blood rheology and coagulation of fresh whole blood or some fraction thereof without adding external reagents. In still other embodiments, PCM device 100 and/or test cartridge 120 are configured for measuring with no functional delay the dynamic balance between pro- and anti-thrombotic hemostatic status by sequential samples from the same person or animal.

Referring now to FIG. 10A and FIG. 10B and to FIG. 11A and FIG. 11B, end views and top down views, respectively, are shown to illustrate more details of disposable blood introduction device 160 in relation to the pair of plate carriers 134 of the presently disclosed test cartridge 120. Disposable blood introduction device 160 may include a grip portion 164 and a funnel portion 166 that includes fluid channel 162. Further, disposable blood introduction device 160 may have an inlet 168 and an outlet 170. As funnel portion 166 is tapered, the opening that is inlet 168 is larger than the opening that is outlet 170. Additionally, a pair of alignment features 172 may be provided on funnel portion 166. When installed, outlet 170 may be fitted into blood introduction channel 140 formed by plate carriers 134A, 134B and with alignment features 172 fitted against plate carriers 134A, 134B. FIG. 12, FIG. 13, and FIG. 14 show various detailed drawings of an example of disposable blood introduction device 160 of the presently disclosed test cartridge 120. All exemplary dimensions shown in FIG. 13 and FIG. 14 are in millimeters (mm). In one example, the diameter of inlet 168 of disposable blood introduction device 160 is about 8 mm, the diameter of outlet 170 is about 1.5 mm, and the narrowest portion of fluid channel 162 has a diameter of about 0.6 mm (see FIG. 14).

Accordingly, disposable blood introduction device 160 can provide a hollow tube of disposable material that includes, in some embodiments: a) an open top (e.g., inlet 168); b) an upper cylindrical portion of funnel portion 166; c) a frustoconical portion of funnel portion 166; d) a lower cylindrical portion of funnel portion 166; d) a flat bottom at outlet 170; and e) a lip (e.g., grip portion 164) attached to the upper cylindrical portion and/or to the frustoconical portion. Further, the wall thickness of funnel portion 166 gradually tapers from inlet 168 to outlet 170. Additionally, disposable blood introduction device 160 can include a solid plug cap (not shown), which is attached to, for example, grip portion 164; wherein the solid plug cap sealingly nests within inlet 168.

Disposable blood introduction device 160 can be formed, for example, of any kind of polymer or glass material that can hold blood and allows the blood at the bottom of the device to move into test cartridge 120 when installed. Disposable material can be sterilized before use. Examples of materials include nylon (polyamide), polycarbonate, polypropylene, polyethylene, polyester, and the like.

In operation, blood is introduced to disposable blood introduction device 160 through inlet 168. Funnel portion 166 and the fluid channel 162 therein go from a larger diameter at the inlet 168 of disposable blood introduction device 160 to a smaller diameter near the outlet 170 of disposable blood introduction device 160. The smaller diameter at the outlet 170 of disposable blood introduction device 160 allows a small amount of blood to move out of disposable blood introduction device 160 at a time and into test cartridge 120, when installed, in a measured manner. Once the blood intake area of test cartridge 120 is full, blood no longer moves from disposable blood introduction device 160 into test cartridge 120. Accordingly, disposable blood introduction device 160 allows the blood to automatically dose into test cartridge 120. In some embodiments, the smaller diameter near the outlet 170 of disposable blood introduction device 160 is small enough so that blood does not move from disposable blood introduction device 160 unless disposable blood introduction device 160 is contacted with the blood intake area of test cartridge 120 (i.e., through capillary action).

For purposes of this disclosure, it should be noted that by "blood" is meant a mixture of whole blood with one or more substances, a fraction of whole blood containing one or more of the constituents of whole blood, a fraction of whole blood mixed with one or more non blood substances, or a purified blood constituent, such as blood platelets or serum, a reconstituted blood preparation, a modified blood sample, or a blood substitute.

Blood can be added to disposable blood introduction device 160 using a pipette tip or a syringe. However, in some embodiments, the blood is added to disposable blood introduction device 160 directly from the body of a subject, such as by using a capillary blood collection (finger prick) method. The finger can be punctured by using any of a variety of puncture or incision devices. In other embodiments, the blood is added to disposable blood introduction device 160 from a storage container, such as from a tube, bottle, and the like, by using an alternative means, such as by using a pipette tip, for example. This may be necessary if the blood is stored before being tested, such as after a venous blood draw, for example. Excess or unused blood is removed by detaching disposable blood introduction device 160 from the test cartridge.

Disposable blood introduction device 160 minimizes excess blood, allows blood to be added without measurement/pipetting and allows removal of excess blood, thereby reducing contamination risk from the unused blood. Therefore, disposable blood introduction device 160 can be used in point-of-care settings, such as in the field, operating room, or in emergency situations.

Referring now to FIG. 15, a side view is shown of an example of a glass-filled thermoplastic polymer rotation mechanism 1500 that can be used in place of the glass-filled thermoplastic polymer plates 122 in the presently disclosed PCM device 100 and/or test cartridge 120. In this example, glass-filled thermoplastic polymer rotation mechanism 1500 comprises a housing 1510 with a central bore 1512 (e.g., a tapered central bore) and an inner rod 1514. Housing 1510 is a glass-filled thermoplastic polymer housing and inner rod 1514 is a glass-filled thermoplastic polymer rod.

Inner rod 1514 can be rotated relative to central bore 1512 in housing 1510. In this embodiment, at least one member of the device is a rod (e.g., inner rod 1514) that can rotate to initiate coagulation. In this case, glass-filled thermoplastic polymer rotation mechanism 1500 can be used for a simple two component test in which blood (e.g., blood sample 190) is sandwiched between housing 1510 and inner rod 1514. Namely, a drop of blood is provided at the inlet of central bore 1512, then the blood flows by capillary action between housing 1510 and inner rod 1514.

The glass-filled thermoplastic polymer inner rod 1514 and the glass-filled thermoplastic polymer housing 1510 rotate relative to each other creating a shear force on the blood and, coupled with the glass activation, allow a clot to be measured by a load cell, electrical resistance, and/or torque measurements. In one example, inner rod 1514 and housing 1510 have a clearance of from about 20 μm to about 200 um. In other embodiments, glass-filled thermoplastic polymer rotation mechanism 1500 further comprises a third member having a third surface spaced an amount sufficient to allow a sample droplet of blood to contact the surface of inner rod 1514 and initiate coagulation.

Referring now to FIG. 16 and FIG. 17, a perspective view and a plan view, respectively, are shown of one example of the physical instantiation of PCM device 100 when holding test cartridge 120. Additionally, FIG. 18 shows a close-up view of a portion of the exemplary PCM device 100 shown in FIG. 16 and FIG. 17. In this example, PCM device 100 comprises a base plate 210 that has multiple through-holes 212. The multiple through-holes 212 can be used, for example, to attach a cover (not shown) or any other mechanisms to base plate 210. Base plate 210 can be formed, for example, of molded plastic or aluminum.

In some embodiments, a pair of alignment blocks 214 are mounted on base plate 210 between which housing 132 of test cartridge 120 can be snuggly fitted. A guide rail mounting bracket 216 that supports a pair of floating linear guide rails 218 that are coupled to a pair of receptacles 220 may also be mounted on base plate 210, wherein the pair of receptacles 220 are designed to physically couple to engagement features 136A, 136B of plate carriers 134A, 134B of test cartridge 120 (see FIG. 18). More details of receptacles 220 and engagement features 136 are shown and described hereinbelow with reference to FIG. 20.

Actuators 118 (e.g., Piezo actuators) may also be mounted on base plate 210 and may be mechanically coupled to receptacles 220 via the floating linear guide rails 218. Further, a pair of proximity sensors 222 (e.g., induction proximity sensors) may be mounted on base plate 210. Proximity sensors 222 may be used to sense the positions of the floating linear guide rails 218. Further, an electronics housing 224 may be mounted on base plate 210. Electronics housing 224 contains any control electronics associated with PCM device 100, such as any of the electronics described hereinabove with reference to FIG. 1.

Referring now to FIG. 19, a perspective view is shown of a portion of PCM device 100 shown in FIG. 16 and FIG. 17, but absent test cartridge 120. Namely, FIG. 19 shows a cavity 226 that may be formed in base plate 210. The footprint of cavity 226 is substantially the same as the shape of housing 132 of test cartridge 120, whereas test cartridge 120 rests in cavity 226 when installed in PCM device 100.

Referring now to FIG. 20, an example is shown of the actuator engagement mechanisms of PCM device 100 shown in FIG. 16 and FIG. 17. Namely, FIG. 20 shows a plan view of an example of one of the receptacles 220. In this example, receptacle 220 has a horseshoe type of shape. Two pinch contact ribs 221 are provided on the two "fingers," respectively, of receptacle 220. Pinch contact ribs 221 ensure reliable engagement with engagement features 136 of plate carriers 134 of test cartridge 120. To further ensure reliable engagement, engagement feature 136 of plate carriers 134 of test cartridge 120 may also include a ridge 137, which provides a point contact with receptacle 220.

Referring now to FIG. 21, a perspective view is shown of another example of a test cartridge 120 that includes glass-filled thermoplastic polymer plates 122.

Referring now to FIG. 22, a perspective view is shown of an example of a dual channel PCM device 2200 for receiving and holding two test cartridges 120. Namely, dual channel PCM device 2200 provides the capability to receive two test cartridges 120 and includes the hardware necessary to run two tests simultaneously.

In some embodiments, dual channel PCM device 2200 includes a housing or assembly 2210 that is designed to receive and process two test cartridges 120. Namely, housing 2210 has a first opening 2212 for receiving the first test cartridge 120A and a second opening 2214 for receiving the second test cartridge 120B. Dual channel PCM device 2200 includes substantially the same components and functionality that is described hereinabove with reference to FIG. 1 and FIG. 16 through FIG. 18, except duplicate components and/or hardware are included in order to support two test cartridges 120 simultaneously. Accordingly, dual channel PCM device 2200 has a first channel (i.e., channel one) and a second channel (i.e., channel two).

Using dual channel PCM device 2200, two tests can be run simultaneously. For example, dual channel PCM device 2200 allows one of two scenarios: (1) a time delayed thrombelastogram relative to a first test (i.e., to make a comparison to evaluate effectiveness of treatment, etc.) or (2) two distinct tests (e.g., thrombelastogram and fibrinogen test, or heparin, other platelet function, etc.). Note that the dual tests may be run simultaneously, at different times, or at overlapping times (i.e. the second test is begun while the first test is running).

Using the single channel PCM device 100 and/or dual channel PCM device 2200, a number of different test cartridges 120 with added "chemistry" for fibrinogen testing (or heparin and other platelet function tests as extras) would allow the emergency trauma, cardiology, and vascular clinicians a full suite of clinical diagnostics relevant to their requirements. One advantage is to be able to run either standard whole venous blood, a parallel fibrinogen test, or a second time delayed standard to monitor therapeutic change/ response.

The ability to run a second test cartridge within the same PCM device (e.g., dual channel PCM device 2200), either with, or without "chemistry," would leverage all the current technology and also provide additional clinical information.

However, this could be more flexible than current technology, and also allow near patient clinical responsiveness to additional diagnostic requirements or to monitor therapeutic response. This would be useful as it would take the functionality and versatility of current devices but truly make it point of care as it would be accessible without the pipetting steps.

Running a second standard sample within the same PCM device adds the ability to see a new curve on the same patient, run either after a therapeutic change—i.e., plasma administration, or a significant change in clinical condition alongside the first trace for direct comparison without stopping the first test or requiring a second PCM device.

Using, for example, dual channel PCM device 2200, the time delayed traces can be displayed on the same screen at the same time. Channel two could also be used to run a cartridge with "chemistry" as previously discussed. The key opportunities for the additional chemistry include:

(1) Fibrinogen is an important test that essentially knocks out all platelet function and therefore tests only clottable protein function. Fibrinogen is increasingly being seen as a key test in establishing patient hemostasis. Additionally, therapeutic interventions are now being based on this test.

(2) Other chemistry tests could include: (a) a tissue factor activated test similar to ExTEM and rapid TEG; (b) a heparinase test to allow comparison of a prolonged test with a heparin excluded sample (this is most useful in cardiac theater but is occasionally of use in other areas); and (c) a platelet function test which is the other test offered as "bolt-ons" for TEG and RoTEM. This could also include function and platelet count tests.

"Bog standard" platelet function analyzers aim to work in a similar way, but some analyzers use chemistry to test specific platelet activation receptor function (ADP, Cyclo ox), which can determine whether aspirin or clopidogrel are actually working. This could also be incorporated within the presently disclosed PCM devices, so long as additional "chemistry" is introduced.

In addition to coagulation tests, non-clotting tests may also be performed. For example, with respect to hemoglobin, the addition of a near patient hemoglobin assay to a thrombelastogram would be very useful to the clinician, as it is currently also requested. It is possible to introduce an optical test through the glass-filled thermoplastic polymer plates 122 on the same sample, which would reduce time lag or the reliance on another near patient test. Further, incorporating a separate assay into the same device would therefore be beneficial.

With respect to blood glucose, blood glucose is often tested in hemorrhage situations, and although the technology is widespread, a combined glucose oxidase electrochemical sensor could provide the information more simply than current practices. Current practice is to either use a separate monitor using capillary blood or measure glucose as part of an arterial blood gas analysis (which, in practice, is not ideal).

With respect to arterial blood gas analysis, arterial blood gas analyzers have moved out of the lab and into the critical care areas over the last 10-15 years. There is an added advantage to the presently disclosed PCM devices in that repeated samples are essentially looked at during major cases in a similar way to repeat clotting.

The presently disclosed PCM Device 100 or 2200 may also be used to conduct Hb and platelet count tests. Using, for example, dual channel PCM device 2200, Hb and platelet count tests can be performed in situ using glass-filled thermoplastic polymer plates 122. Advantages include: (1) an optical check can be performed on the exact sample for coagulation, (2) it eliminates variation between blood draw/fingerstick-venous-arterial/non-pipetting, (3) it eliminates the need for additional tests (e.g., lab tests or hemocue), (4) anemia/vascular packers, and (5) platelet count test (also using optical plates 122).

Referring now to FIG. 23, a flow diagram is presented of an example of a method 2300 of measuring coagulation response in a blood sample using, for example, PCM device 100 and test cartridge 120. Method 2300 may include, but is not limited to, the following steps.

At a step 2310, a sample droplet of blood is placed between and in contact with the first and second facing surfaces of oppositely disposed glass-filled thermoplastic polymer plates 122 of test cartridge 120. In one example, disposable blood introduction device 160 is used to place the blood sample between glass-filled thermoplastic polymer plates 122A and 122B.

At a step 2315, at least one glass-filled thermoplastic polymer plate 122 is moved linearly with respect to the other glass-filled thermoplastic polymer plate 122 at a predetermined speed sufficient to activate platelets through exposure to shear forces. In one example, actuator 118A of PCM device 100 is used to move glass-filled thermoplastic polymer plate 122A linearly with respect to glass-filled thermoplastic polymer plate 122B at a predetermined speed sufficient to activate platelets through exposure to shear forces. In another example, actuator 118B of PCM device 100 is used to move glass-filled thermoplastic polymer plate 122B linearly with respect to glass-filled thermoplastic polymer plate 122A at a predetermined speed sufficient to activate platelets through exposure to shear forces. In yet another example, actuators 118A and 118B of PCM device 100 are used to move both glass-filled thermoplastic polymer plates 122A and 122B linearly with respect to each other at a predetermined speed sufficient to activate platelets through exposure to shear forces.

At a step 2320, using, for example, optics system 114 of PCM device 100, an optical detection operation is performed (i.e., via measurement of mechanical displacement) of the interaction between the surfaces of glass-filled thermoplastic polymer plates 122A, 122B, resulting from changes in the viscosity of the sample fluid and binding to the surfaces in order to measure coagulation response of the droplet of blood.

Referring now to FIG. 24, a flow diagram is presented of a method 2400, which is another example of a method of measuring coagulation response in a blood sample using, for example, PCM device 100 and test cartridge 120. Method 2400 may include, but is not limited to, the following steps.

At a step 2410, a sample droplet of blood is placed between and in contact with the first and second facing surfaces of the oppositely disposed glass-filled thermoplastic polymer plates 122 of test cartridge 120. In one example, disposable blood introduction device 160 is used to place the blood sample between glass-filled thermoplastic polymer plates 122A and 122B.

At a step 2415, at least one glass-filled thermoplastic polymer plate 122 is moved linearly with respect to the other glass-filled thermoplastic polymer plate 122 at a first speed. In one example, actuator 118A of PCM device 100 is used to move glass-filled thermoplastic polymer plate 122A linearly with respect to glass-filled thermoplastic polymer plate 122B at a first speed. In another example, actuator 118B of PCM device 100 is used to move glass-filled thermoplastic polymer plate 122B linearly with respect to glass-filled thermoplastic polymer plate 122A at a first speed. In yet another example, actuators 118A and 118B of PCM device 100 are used to move both glass-filled thermoplastic polymer plates 122A and 122B linearly with respect to each other at a first speed.

At a step 2420, using, for example, optics system 114 of PCM device 100, a first coagulation response of the blood indicative of platelet response in the blood is optically detected.

At a step 2425, at least one glass-filled thermoplastic polymer plate 122 is moved linearly with respect to the other glass-filled thermoplastic polymer plate 122 at a second speed. In one example, actuator 118A of PCM device 100 is used to move glass-filled thermoplastic polymer plate 122A linearly with respect to glass-filled thermoplastic polymer plate 122B at a second speed. In another example, actuator 118B of PCM device 100 is used to move glass-filled thermoplastic polymer plate 122B linearly with respect to glass-filled thermoplastic polymer plate 122A at a second speed. In yet another example, actuators 118A and 118B of PCM device 100 are used to move both glass-filled thermoplastic polymer plates 122A and 122B linearly with respect to each other at a second speed.

At a step 2430, using, for example, optics system 114 of PCM device 100, a second coagulation response of the blood indicative of fibrin polymerization is optically detected.

In method 2300 of FIG. 23 and/or method 2400 of FIG. 24, to detect two different types of coagulation response, glass-filled thermoplastic polymer plates 122 can be moved relative to each other at a first speed and a response optically detected, and thereafter moved at a second speed which is slower than the first speed and a second response optically detected, typically fibrin polymerization. In addition, in the case where only one glass-filled thermoplastic polymer plate 122 is moved, it should be appreciated that the visco elastic response of the blood sample on the surfaces of both glass-filled thermoplastic polymer plates 122 can cause the movement of the first glass-filled thermoplastic polymer plate 122 to induce movement of the second glass-filled thermoplastic polymer plate 122 ("coupled motion"), which can be measured as indicative of visco elastic response of the blood, ultimately leading to conclusions which may be inferred relative to coagulation response. Moreover, by moving glass-filled thermoplastic polymer plates 122 at different speeds over time, changes in the visco elastic state of the blood sample may be measured as a clot is formed, which is also indicative of coagulation response.

In some embodiments, method 2300 of FIG. 23 and/or method 2400 of FIG. 24 include moving one glass-filled thermoplastic polymer plate 122 relative to the other glass-filled thermoplastic polymer plate 122 in a manner causing the other glass-filled thermoplastic polymer plate 122 to move because of visco elastic coupling between the blood and the other glass-filled thermoplastic polymer plate 122; and determining the visco elastic properties of the blood from the movement of the other glass-filled thermoplastic polymer plate 122. In other embodiments, the method further includes detecting strain rates caused by movement of the one glass-filled thermoplastic polymer plate 122 and the other glass-filled thermoplastic polymer plate 122 caused by visco elastic coupling between the one glass-filled thermoplastic polymer plate 122 and the other glass-filled thermoplastic polymer plate 122 caused by the blood sample; and determining the coagulation state of the blood by inference analysis based on visco elasticity of the blood sample determined from mechanical coupling between the two glass-filled thermoplastic polymer plates 122 and the resulting strain rates. In still other embodiments, method 2300 of FIG. 23 and/or method 2400 of FIG. 24 further include continually measuring the visco elasticity of the blood over time to monitor changes over time of the coagulation response of the blood. In some embodiments, the sample droplet of blood comes directly from the body of a subject.

In other embodiments, PCM device 100, dual channel PCM device 2200, and/or test cartridge 120 can be used in measurement of the viscosity of a multitude of fluids other than blood, including non-biological fluids. For example, using devices and methods similar to those taught herein, the viscosity of any number of other fluids, including non-biological fluids, can be measured for significantly less than current measurement methods.

Referring now to FIG. 25 is a flow diagram of an example of a method 2500 of introducing blood into a test cartridge (e.g., test cartridge 120) using the presently disclosed disposable blood introduction device 160. Method 2500 may include, but is not limited to, the following steps.

At a step 2510, the disposable blood introduction device 160 of the present invention is inserted into test cartridge 120. For example, the outlet end 170 of disposable blood introduction device 160 is inserted into blood introduction channel 140 formed by the arrangement of plate carriers 134A, 134B in test cartridge 120.

At a step 2515, a droplet of blood is inserted into inlet 168 of disposable blood introduction device 160 and then the blood flows into fluid channel 162 of disposable blood introduction device 160 by capillary action.

At a step 2520, the blood is allowed to move from disposable blood introduction device 160 into test cartridge 120 until the blood stops moving. Namely, by capillary action blood flows from disposable blood introduction device 160 into the gap between glass-filled thermoplastic polymer plates 122A, 122B of test cartridge 120. When the gap between glass-filled thermoplastic polymer plates 122A, 122B is filled with blood, the blood flow from disposable blood introduction device 160 automatically stops.

At a step 2525, disposable blood introduction device 160 is removed from test cartridge 120 after the blood has stopped moving into test cartridge 120.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A device for measuring coagulation response in a blood sample, the device comprising a test cartridge comprising:
    a first member having a first flat surface; and
    a second member having a second flat surface positioned to face the first flat surface to define a space therebetween sized to allow a sample of blood to be introduced into the space to contact the first flat surface and the second flat surface, the first member configured to linearly move and oscillate to cause the first flat surface to oscillate relative to the second flat surface to cause the sample of blood to coagulate and bind thereto, the second member configured to move from a stationary configuration responsive to the movement of the first member via the coagulated sample of blood, thereby changing mechanical displacement between the first and second members for measuring a coagulation response of the sample of blood.

2. The device of claim 1, wherein the test cartridge is configured to be disposable after use.

3. The device of claim 1, further comprising a humidity control mechanism.

4. The device of claim 3, wherein the humidity control mechanism comprises a sponge-like pad inside a humidity pouch, and wherein the humidity pouch comprises a removable cover.

5. The device of claim 4, wherein the removable cover is configured to be removed to expose the sponge-like pad to an interior environment of the test cartridge.

6. The device of claim 1, further comprising a temperature control mechanism configured to maintain a desired temperature within the device.

7. The device of claim 6, wherein the temperature control mechanism comprises a heater.

8. The device of claim 6, wherein the temperature control mechanism comprises a cooling device.

9. The device of claim 1, wherein the test cartridge is configured to be coupled to a measuring device, and wherein the first member further comprises an engagement feature configured to engage with a drive mechanism in the measuring device.

10. The device of claim 9, wherein the engagement feature comprises one or more of pinch contact ribs or ridges.

11. The device of claim 1, further comprising a receptacle configured to provide a path for the sample of blood to pass from a blood introduction mechanism to the space between the first flat surface and the second flat surface.

12. The device of claim 11, further comprising the blood introduction mechanism, wherein the blood introduction mechanism comprises:
    an open top comprising a first opening;
    a funnel portion;
    a flat bottom comprising a second opening smaller than the first opening; and
    a lip attached to the funnel portion,
    wherein a desired amount of blood introduced to the open top is configured to pass through the blood introduction mechanism and into the receptacle of the test cartridge, thereby providing the sample of blood into the test cartridge.

13. The device of claim 1, wherein the first and second members comprise a glass-filled thermoplastic polymer.

14. The device of claim 1, wherein the first and second flat surfaces are each entirely flat.

15. The device of claim 14, wherein the first member comprises a first round plate, wherein the second member comprises a second round plate, and wherein the first flat surface is disposed on the first round plate and the second flat surface is disposed on the second round plate.

16. The device of claim 1, wherein the first flat surface and the second flat surface are parallel.

17. The device of claim 1, wherein the mechanical displacement between the first and second members is configured to be optically detected for measuring the coagulation response of the sample of blood.

18. The device of claim 1, wherein mechanical displacement between the first and second members decreases as binding between the first and second flat surfaces increases resulting from increased strength in clotting of the sample of blood.

19. The device of claim 1, further comprising a measuring device configured to be removably coupled to the test cartridge.

20. The device of claim 19, wherein the measuring device comprises a drive mechanism configured to be coupled to the first member to cause the first flat surface to oscillate relative to the second flat surface.

21. The device of claim 20, wherein the drive mechanism comprises a motor configured to move the first member.

22. The device of claim 21, wherein the motor comprises a piezo motor.

23. The device of claim 21, further comprising a processor connected to the motor and configured to control operation of the motor in a predetermined manner.

24. The device of claim 19, wherein the measuring device further comprises a second drive mechanism configured to be coupled to the second member to cause the second flat surface to move.

25. The device of claim 19, wherein the measuring device comprises one or more optical sensors configured to measure information indicative of the coagulation response of the sample of blood.

26. The device of claim 19, wherein the measuring device comprises a display configured to display information related to the coagulation response of the sample of blood.

27. The device of claim 19, wherein the measuring device comprises a communications interface configured to wirelessly transmit information from the measuring device.

28. The device of claim 19, wherein the measuring device is configured to continually measure visco elasticity of the sample of blood over time to monitor changes over time of the coagulation response of the sample of blood.

29. The device of claim 1, wherein the first member is configured to be moved at a first speed to permit optical detection related to binding of the sample of blood to the first and second flat surfaces to determine platelet response during coagulation.

30. The device of claim 29, wherein the first member is configured to be subsequently moved at a second speed slower than the first speed to permit optical detection of a level of coagulation of the sample of blood as indicative of a fibrin polymerization response.

31. The device of claim 1, further comprising one or more pull tabs configured to be removed from the test cartridge before the sample of blood is introduced.

32. The device of claim 1, further comprising memory configured to store information about the coagulation response.

33. The device of claim 1, wherein the second member is configured to move relative to the first member in a manner causing the second member to move due to visco elastic coupling between the sample of blood and the first and second flat surfaces, and wherein visco elastic properties of the sample of blood are determined from the movement of the second member.

34. The device of claim 1, wherein strain rates are configured to be detected by movement of the second member relative to the first member caused by visco elastic coupling between the first and second flat surfaces caused by the sample of blood, and wherein the coagulation response is determined by an inference analysis based on visco elasticity of the sample of blood determined from mechanical coupling between the first and second flat surfaces and the detected strain rates.

* * * * *